(12) United States Patent
Menge et al.

(10) Patent No.: US 7,494,990 B2
(45) Date of Patent: Feb. 24, 2009

(54) 2-(PIPERIDIN-4-YL)-4,5-DIHYDRO-2H-PYRIDAZIN-3-ONE DERIVATIVES AS PDE4 INHIBITORS

(75) Inventors: Wiro M. P. B. Menge, HM Arnhem (NL); Geert Jan Sterk, JJ Utrecht (NL)

(73) Assignee: NYCOMED GmbH, Constance (DE)

( * ) Notice: Subject to any disclaimer, the term of this patent is extended or adjusted under 35 U.S.C. 154(b) by 20 days.

(21) Appl. No.: 10/587,836

(22) PCT Filed: Feb. 1, 2005

(86) PCT No.: PCT/EP2005/050415

§ 371 (c)(1), (2), (4) Date: Aug. 16, 2006

(87) PCT Pub. No.: WO2005/075456

PCT Pub. Date: Aug. 18, 2005

(65) Prior Publication Data

US 2007/0179146 A1 Aug. 2, 2007

(30) Foreign Application Priority Data

Feb. 4, 2004 (EP) .................................. 04002420

(51) Int. Cl.
| | |
|---|---|
| A61K 31/55 | (2006.01) |
| A61K 31/541 | (2006.01) |
| A61K 31/5355 | (2006.01) |
| A61K 31/501 | (2006.01) |
| C07D 401/04 | (2006.01) |
| C07D 411/02 | (2006.01) |
| C07D 413/02 | (2006.01) |
| C07D 417/02 | (2006.01) |
| C07D 273/01 | (2006.01) |
| C07D 237/04 | (2006.01) |
| C07D 241/04 | (2006.01) |
| C07D 241/08 | (2006.01) |
| A61P 9/00 | (2006.01) |
| C07D 307/87 | (2006.01) |
| C07C 62/38 | (2006.01) |
| C07C 65/32 | (2006.01) |

(52) U.S. Cl. .............................. 514/217.05; 514/227.8; 514/236.5; 514/252.02; 514/252.03; 540/524; 544/6; 544/7; 544/70; 544/114; 544/230; 544/238; 549/462; 562/459; 562/463

(58) Field of Classification Search ................. 540/524; 544/60, 114, 238, 7, 70, 230; 514/217.05, 514/227.8, 236.5, 252.02, 252.03

See application file for complete search history.

(56) References Cited

U.S. PATENT DOCUMENTS

| | | | |
|---|---|---|---|
| 5,267,027 A | 11/1993 | Ugaki et al. |
| 5,434,149 A | 7/1995 | Jonas et al. |
| 5,747,489 A | 5/1998 | Jonas et al. |
| 5,859,008 A | 1/1999 | Jonas et al. |
| 6,103,718 A | 8/2000 | Sterk |
| 6,225,303 B1 | 5/2001 | Miller et al. |
| 6,380,196 B1 | 4/2002 | Ulrich et al. |
| 6,399,611 B1 | 6/2002 | Jonas et al. |
| 6,544,993 B1 | 4/2003 | Sterk |
| 6,756,371 B1 | 6/2004 | Sterk |
| 6,933,296 B2 | 8/2005 | Sterk |
| 6,953,853 B2 | 10/2005 | Grundler et al. |
| 7,022,696 B2 | 4/2006 | Grundler et al. |
| 2004/0127707 A1 | 7/2004 | Sterk |
| 2006/0094710 A1 | 5/2006 | Sterk |
| 2006/0166995 A1 | 7/2006 | Sterk |
| 2006/0167001 A1 | 7/2006 | Sterk |

FOREIGN PATENT DOCUMENTS

| | | |
|---|---|---|
| EP | 0 539 806 A1 | 5/1993 |
| EP | 0 618 201 A1 | 10/1994 |
| EP | 0 723 962 A1 | 7/1996 |
| EP | 0 738 715 A2 | 10/1996 |
| EP | 0 763 534 A1 | 3/1997 |
| WO | 93/07146 A1 | 4/1993 |
| WO | 98/31674 A1 | 7/1998 |
| WO | 99/31071 A1 | 6/1999 |
| WO | 99/31090 A1 | 6/1999 |
| WO | 99/47505 A1 | 9/1999 |
| WO | 01/19818 A1 | 3/2001 |
| WO | 01/30766 A1 | 5/2001 |
| WO | 01/30777 A1 | 5/2001 |
| WO | 01/94319 A1 | 12/2001 |
| WO | 02/064584 A1 | 8/2002 |

(Continued)

OTHER PUBLICATIONS

Dyke, et al., Exp. Opin. Invest. Drugs 8:1301-1325 (1999).*

(Continued)

*Primary Examiner*—Mark L Berch
*Assistant Examiner*—Cecilia M Jaisle
(74) *Attorney, Agent, or Firm*—The Nath Law Group; Joshua B. Goldberg; Sheldon M. McGee

(57) ABSTRACT

The compounds of a certain formula (1),

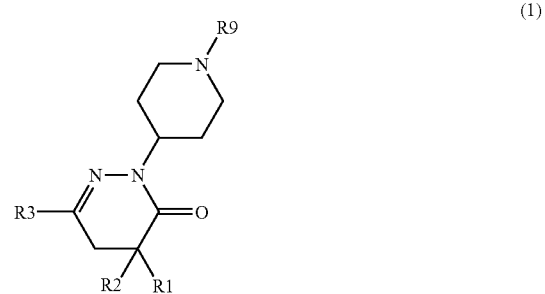

in which R1, R2, R3 and R9 have the meanings as given in the description, are novel effective PDE4 inhibitors.

14 Claims, No Drawings

FOREIGN PATENT DOCUMENTS

| WO | 02/085885 A1 | 10/2002 |
|---|---|---|
| WO | 02/085906 A2 | 10/2002 |
| WO | 03/032993 A1 | 4/2003 |
| WO | WO 2004018451 * | 8/2003 |
| WO | 2004/017957 A1 | 3/2004 |
| WO | 2004/017974 A1 | 3/2004 |
| WO | 2004/018449 A1 | 3/2004 |
| WO | 2004/018450 A1 | 3/2004 |
| WO | 2004/018451 A1 | 3/2004 |
| WO | 2005/075437 A1 | 8/2005 |
| WO | 2005/075457 A1 | 8/2005 |

OTHER PUBLICATIONS

Hanifin, et al., Journal of Investigative Dermatology, 107(1):51-56 (1996).*
MacKenzie, Alergology International (2004) 53:101-110.*
Sasaki, et al., Inflamm. Res., 53 (2004), 031-037.*
European Respiratory Society, Feb. 13, 2007, http://www.newtocopd.com/currentaffairsnews/list751_item17680.aspx, downloaded Jan. 16, 2008.*
Lipworth, Lancet, vol. 365: Iss. 9454, 167-175, 2005.*
Barnes, Thorax, 2003: 58, pp. 803-808.*
Dyke, Exp. Opin. Invest. Drugs (1999) 8(9), 1301-1325.*
Kawasaki, et al., Allergology International, vol. 54, No. 3, 2005, pp. 427-433 (abst.).*
Baumer, et al., Inflamm Allergy Drug Targets, Mar. 2007; 6(1), 17-26 (abst.).*
Coates, W.J., et al., "1,4-Bis (3-oxo-2,3-dihydropyridazin-6-yl)benzene Analogues: Potent Phosphodiesterase Inhibitors and Inodilators", *J. Med. Chem.*, vol. 33, pp. 1735-1741, (1990).
Van der Mey, M., et al., "Relationships of 4-Aryl-Substituted *cis*-Tetra- and *cis*-Hexahydrophthalazinones", *J. Med. Chem.*, vol. 44, No. 16, pp. 2523-2535, (2001).
Van der Mey, M., et al., "Novel Selective PDE4 Inhibitors. 1. Synthesis, Structure-Activity Relationships, and Molecular Modeling of 4-(3,4-Dimethoxyphenyl)-2*H*-phthalazin-1-ones and Analogues", *J. Med. Chem.*, vol. 44, No. 16, pp. 2511-2522, (2001).
Van der Mey, M., et al., "Novel Selective PDE4 Inhibitors. 3. In Vivo Antiinfalammatory Activity of a New Series of N-Substituted *cis*-Tetra- and *cis*-Hexahydrophthalazinones", *J. Med. Chem.*, vol. 45, No. 12, pp. 2520-2525, (2002).
Van der Mey, M., et al., "Novel Selective Phosphodiesterase (PDE4) Inhibitors. 4. Resolution, Absolute Configuration, and PDE4 Inhibitory Activity of *cis*-Tetra- and *cis*-Hexahydrophthalazinones", *J. Med. Chem.*, vol. 45, No. 12, pp. 2526-2533, (2002).
Norman, P., "PDE4 inhibitors 2001. Patent and literature activity 2000—Sep. 2001", *Expert Opin. Ther. Patents*, vol. 12, No. 1, pp. 93-111, (2002).
Grootendorst, et al. "Selective phosphodiesterase inhibitors for the treatment of asthma and chronic obstructive pulmonary disease", *Current Opinion in Allergy and Clinical Immunology*, (2002), vol. 2, pp. 61-67.
Souness, et al. "Immunosuppresive and anti-inflammatory effects of cyclic AMP phosphodiesterase (PDE) type 4 inhibitors", *Immunopharmacology* 47 (2000) pp. 127-162.

\* cited by examiner

2-(PIPERIDIN-4-YL)-4,5-DIHYDRO-2H-PYRIDAZIN-3-ONE DERIVATIVES AS PDE4 INHIBITORS

This application was filed under 35 U.S.C. 371 as a national stage of PCT/EP2005/050415, filed Feb. 1, 2005.

FIELD OF APPLICATION OF THE INVENTION

The invention relates to novel pyridazinone-derivatives, which are used in the pharmaceutical industry for the production of pharmaceutical compositions.

KNOWN TECHNICAL BACKGROUND

International Patent Applications WO98/31674 (=U.S. Pat. No. 6,103,718), WO99/31071, WO99/31090, WO99/47505 (=U.S. Pat. No. 6,255,303), WO01/19818, WO01/30766, WO01/30777, WO01/94319, WO02/064584, WO02/085885 and WO02/085906 disclose phthalazinone derivatives having PDE4 inhibitory properties. In the International Patent Application WO03/032993, the European Patent Applications EP 539806, EP 618201, EP 723962, EP 738715, EP 763534 and in the German Patent Application DE19604388 arylalkyldiazinone and thiadiazinone derivatives are described as PDE4 inhibitors. International Patent Application WO93/07146 (=U.S. Pat. No. 5,716,954) discloses benzo and pyrido pyridazinone and pyridazinthione compounds with PDE4 inhibiting activity.

In the Journal of Medicinal Chemistry, Vol. 33, No. 6, 1990, pp. 1735-1741 1,4-Bis(3-oxo-2,3-dihydro-pyridazin-6-yl)benzene derivatives are described as potent phosphodiesterase inhibitors and inodilators. In the Journal of Medicinal Chemistry Vol. 45 No. 12, 2002, pp. 2520-2525, 2526-2533 and in Vol. 44, No. 16, 2001, pp. 2511-2522 and pp. 2523-2535 phthalazinone derivatives are described as selective PDE4 inhibitors.

DESCRIPTION OF THE INVENTION

It has now been found that the pyridazinone-derivatives, which are described in greater details below, have surprising and particularly advantageous properties.

The invention thus relates to compounds of formula 1

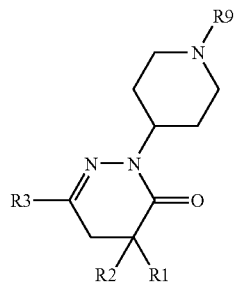
(1)

in which
R1 is 1-4C-alkyl and
R2 is 1-4C-alkyl,
R3 represents a phenyl derivative of formulae (a) or (b)

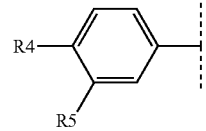
(a)

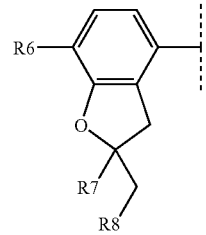
(b)

wherein
R4 is 1-4C-alkoxy or 1-4C-alkoxy which is completely or predominantly substituted by fluorine,
R5 is 1-8C-alkoxy, 3-7C-cycloalkoxy, 3-7C-cycloalkylmethoxy, or 1-4C-alkoxy which is completely or predominantly substituted by fluorine,
R6 is 1-4-alkoxy, 3-5C-cycloalkoxy, 3-5C-cycloalkylmethoxy, or 1-4C-alkoxy which is completely or predominantly substituted by fluorine,
R7 is 1-4C-alkyl and
R8 is hydrogen or 1-4C-alkyl,
or wherein
R7 and R8 together and with inclusion of the two carbon atoms, to which they are bonded, form a spiro-linked 5-, 6- or 7-membered hydrocarbon ring, optionally interrupted by an oxygen or sulphur atom,
R9 is —C(O)R10, —S(O)$_2$—R14, —(CH$_2$)$_n$—C(O)—R18 or —C(O)—(CH$_2$)$_m$—R21,
R10 is 1-4C-alkyl, —N(R11)R12, phenyl or phenyl substituted by R13,
R11 is hydrogen, 1-4C-alkyl, 3-7C-cycloalkyl or 3-7C-cycloalkylmethyl,
R12 is hydrogen, 1-4C-alkyl, 3-7C-cycloalkyl or 3-7C-cycloalkylmethyl,
or R11 and R12 together and with inclusion of the nitrogen atom to which they are bonded, form a 1-pyrrolidinyl-, 1-piperidinyl-, 1-piperazinyl, 1-(1-4C-alkyl)-piperazin-4-yl-, 1-hexahydroazepinyl-, 4-morpholinyl-, 4-thiomorpholinyl-, thiomorpholin-1-oxide-4-yl- or thiomorpholin-1,1-dioxide-4-yl-ring,
R13 is hydroxyl, halogen, nitro, cyano, hydroxycarbonyl, 1-4C-alkyl, trifluoromethyl, 1-4C-alkoxy, 1-4C-alkoxy which is completely or predominantly substituted by fluorine, 1-4C-alkoxycarbonyl, amino, mono- or di-1-4C-alkylamino, aminocarbonyl, mono- or di-1-4C-alkylaminocarbonyl, 1-4C-alkylcarbonyl, 1-4C-alkylcarbonylamino or 1-4C-alkylcarbonyloxy,
R14 is 1-4C-alkyl, —N(R15)R16, phenyl or phenyl substituted by R17,
R15 is hydrogen, 1-4C-alkyl, 3-7C-cycloalkyl or 3-7C-cycloalkylmethyl,
R16 is hydrogen, 1-4C-alkyl, 3-7C-cycloalkyl or 3-7C-cycloalkylmethyl,
or R15 and R16 together and with inclusion of the nitrogen atom to which they are bonded, form a 1-pyrrolidinyl-, 1-piperidinyl-, 1-piperazinyl, 1-(1-4C-alkyl)-piperazin4- yl-, 1-hexahydroazepinyl-, 4-morpholinyl, 4-thiomorpholinyl-, thiomorpholin-1-oxide-4-yl- or thiomorpholin-1,1-dioxide-4yl-ring, R17 is hydroxyl, halogen, nitro, cyano, carboxyl, 1-4C-alkyl, trifluoromethyl, 1-4C-alkoxy, 1-4C-alkoxy which is completely or predominantly substituted by fluorine, 1-4C-alkoxycarbonyl, amino, mono- or di-1-4C-alkylamino, aminocarbonyl, mono- or di-1-4C-alkylaminocarbonyl, 1-4C-alkylcarbonyl, 1-4C-alkylcarbonylamino or 1-4C-alkylcarbonyloxy, R18 is —N(R19)R20, R19 is hydrogen, 1-4C-alkyl, 3-7C-cycloalkyl or 3-7C-cycloalkylmethyl, R20 is hydrogen, 1-4C-alkyl, 3-7C-cycloalkyl or 3-7C-cycloalkylmethyl, or R19 and R20 together and with inclusion of the nitrogen atom to which they are bonded, form a 1-pyrrolidinyl-, 1-piperidinyl-, 1-piperazinyl, 1-(1-4C-alkyl)-piperazin4-yl-, 1-hexahydroazepinyl-, 4-morpholinyl, 4-thiomorpholinyl-, thiomorpholin-1-oxide-4-yl- or thiomorpholin-1,1-dioxide-4-yl-ring, R21 is —N(R22)R23, R22 is hydrogen, 1-4C-alkyl, 3-7C-cycloalkyl or 3-7C-cycloalkylmethyl, R23 is hydrogen, 1-4C-alkyl, 3-7C-cycloalkyl or 3-7C-cycloalkylmethyl, or R22 and R23 together and with inclusion of the nitrogen atom to which they are bonded, form a 1-pyrrolidinyl-, 1-piperidinyl-, 1-piperazinyl, 1-(1-4C-alkyl)-piperazin4-yl-, 1-hexahydroazepinyl-, 4-morpholinyl, 4-thiomorpholinyl-, thiomorpholin-1-oxide-4-yl-, thiomorpholin-1,1-dioxide4-yl-, pyrrolidin-2,5-dione-1-yl-, morpholin-3,5-dione4-yl-, piperidin-2,6-dione-1-yl, 4,4-dimethylpiperidin-2,6-dione-1-yl or a 1-methyl-imidazolidine-2,4dione-3-yl-ring or a isoindol-1,3-dione-2-yl-ring-system, n is an integer from 1 to 4, m is an integer from 1 to 4, and the salts of these compounds.

1-4C-Alkyl is a straight-chain or branched alkyl radical having 1 to 4 carbon atoms. Examples are the butyl, isobutyl, sec-butyl, tert-butyl, propyl, isopropyl, ethyl and methyl radicals.

1-4C-Alkoxy is a radical which, in addition to the oxygen atom, contains a straight-chain or branched alkyl radical having 1 to 4 carbon atoms. Alkoxy radicals having 1 to 4 carbon atoms which may be mentioned in this context are, for example, the butoxy, isobutoxy, sec-butoxy, tertbutoxy, propoxy, iso-propoxy, ethoxy and methoxy radicals.

1-8C-Alkoxy is a radical which, in addition to the oxygen atom, contains a straight-chain or branched ally radical having 1 to 8 carbon atoms. Alkoxy radicals having 1 to 8 carbon atoms which may be mentioned in this context are, for example, the octyloxy, heptyloxy, isoheptyloxy (5-methylhexyloxy), hexyloxy, isohexyloxy (4-methylpentyloxy), neohexyloxy (3,3-dimethylbutoxy), pentyloxy, isopentyloxy (3-methylbutoxy), neopentyloxy (2,2-dimethylpropoxy), butoxy, isobutoxy, sec-butoxy, tert-butoxy, pro-poxy, isopropoxy, ethoxy and methoxy radicals.

1-4C-Alkoxy which is completely or predominantly substituted by fluorine is, for example, the 2,2,3,3,3-pentafluoropropoxy, the perfluoroethoxy, the 1,2,2-trifluoroethoxy and in particular the 1,1,2,2-tetrafluoroethoxy, the 2,2,2-trifluoroethoxy, the trifluoromethoxy and the difluoromethoxy radical, of which the difluoromethoxy radical is preferred. "Predominantly" in this connection means that more than half of the hydrogen atoms of the 1-4C-alkoxy group are replaced by fluorine atoms.

3-7C-Cycloalkoxy stands for cyclopropyloxy, cyclobutyloxy, cyclopentyloxy, cyclohexyloxy or cycloheptyloxy, of which cyclopropyloxy, cyclobutyloxy and cyclopentyloxy are preferred.

3-7C-Cycloalkylmethoxy stands for cyclopropylmethoxy, cyclobutylmethoxy, cyclopentylmethoxy, cyclohexylmethoxy or cycloheptylmethoxy, of which cyclopropylmethoxy, cyclobutylmethoxy and cyclopentylmethoxy are preferred.

3-5C-Cycloalkoxy stands for cyclopropyloxy, cyclobutyloxy and cyclopentyloxy.

3-5C-Cycloalkylmethoxy stands for cyclopropylmethoxy, cyclobutylmethoxy and cyclopentylmethoxy.

As spiro-linked 5-, 6- or 7-membered hydrocarbon rings, optionally interrupted by an oxygen or sulphur atom, may be mentioned the cyclopentane, cyclohexane, cycloheptane, tetrahydrofuran, tetrahydropyran and the tetrahydrothiophen ring.

Halogen within the meaning of the present invention is bromine, chlorine or fluorine.

1-4C-Alkoxycarbonyl is a carbonyl group to which one of the abovementioned 1-4C-alkoxy radicals is bonded. Examples are the methoxycarbonyl $[CH_3O—C(O)—]$ and the ethoxycarbonyl $[CH_3CH_2O—C(O)—]$ radical. Mono- or Di-1-4C-alkylamino radicals contain in addition to the nitrogen atom, one or two of the above-mentioned 1-4C-alkyl radicals.

Mono- or Di-1-4C-alkylaminocarbonyl radicals contain in addition to the carbonyl group one of the above-mentioned mono- or di-1-4C-alkylamino radicals. Examples which may be mentioned are the N-methyl- the N,N-dimethyl-, the N-ethyl-, the N-propyl-, the N,N-diethyl- and the N-isopropylaminocarbonyl radical.

1-4C-Alkylcarbonyl is a carbonyl group to which one of the abovementioned 1-4C-alkyl radicals is bonded. An example is the acetyl radical $[CH_3C(O)—]$.

An 1-4C-Alkylcarbonylamino radical is, for example, the propionylamino $[C_3H_7C(O)NH—]$ and the acetylamino radical $[CH_3C(O)NH—]$ 1-4C-Alkylcarbonyloxy stands for a carbonyloxy group to which one of the abovementioned 1-4C-alkyl radicals is bonded. An example is the acetoxy radical $[CH_3C(O)—O—]$.

3-7C-Cycloalkyl stands for cyclopropyl, cyclobutyl, cyclopentyl, cyclohexyl or cycloheptyl, of which cyclopropyl and cyclopentyl are preferred 3-7C-Cycloalkylmethyl stands for cyclopropylmethyl, cyclobutylmethyl, cyclopentylmethyl, cyclohexylmethyl or cycloheptylmethyl.

Suitable salts for compounds of formula 1 are—depending on substitution—all acid addition salts or all salts with bases. Particular mention may be made of the pharmacologically tolerable inorganic and organic acids and bases customarily used in pharmacy. Those suitable are, on the one hand, water-soluble and water-insoluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl) benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3hydroxy-2-naphthoic acid, the acids being employed in salt preparation—depending on whether a mono- or polybasic acid is concerned and depending on which salt is desired—in an equimolar quantitative ratio or one differing therefrom.

On the other hand salts with bases are—depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds according to the invention on an industrial scale, are converted into pharmacologically tolerable salts by processes known to the person skilled in the art.

According to expert's knowledge the compounds of the invention as well as their salts may contain, e.g. when isolated in crystalline form, varying amounts of solvents. Included within the scope of the invention are therefore all solvates and in particular all hydrates of the compounds of formula 1 as well as all solvates and in particular all hydrates of the salts of the compounds of formula 1.

An embodiment (embodiment A) of the invention are those compounds of formula 1 in which
R1 is 1-4C-alkyl,
R2 is 1-4C-alkyl,
R3 represents a phenyl derivative of formulae (a) or (b)

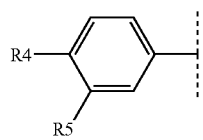

(a)

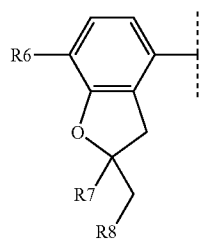

(b)

wherein
R4 is 1-2C-alkoxy or 1-2C-alkoxy which is completely or predominantly substituted by fluorine,
R5 is 1-2C-alkoxy or 1-2C-alkoxy which is completely or predominantly substituted by fluorine,
R6 is 1-2C-alkoxy or 1-2C-alkoxy which is completely or predominantly substituted by fluorine,
R7 is methyl and
R8 is hydrogen,
or wherein
R7 and R8 together and with inclusion of the two carbon atoms, to which they are bonded, form a spiro-linked cyclopentane, cyclohexane, tetrahydrofuran ortetrahydropyran ring,
R9 is —C(O)—R10, —S(O)$_2$—R14, —(CH$_2$)$_n$—C(O)—R18 or —C(O)—(CH$_2$)$_m$—R21,
R10 is phenyl or phenyl substituted by R13,
R13 is 1-4C-alkyl or 1-4C-alkoxy,
R14 is —N(R15)R16, phenyl or phenyl substituted by R17,
R15 is hydrogen or 1-4C-alkyl,
R16 is hydrogen or 1-4C-alkyl,
R17 is halogen, nitro, cyano, 1-4C-alkyl, 1-4C-alkoxy or 1-4C-alkoxy which is completely or predominantly substituted by fluorine,
R18 is —N(R19)R20,
R19 is hydrogen or 1-4C-alkyl,
R20 is hydrogen or 1-4C-alkyl,
or R19 and R20 together and with inclusion of the nitrogen atom to which they are bonded, form a 1-pyrrolidinyl-, 1-piperidinyl-, 1-piperazinyl, 1-(1-4C-alkyl)-piperazin4-yl-, 1-hexahydroazepinyl-, 4-morpholinyl or 4-thiomorpholinyl-ring,
R21 is —N(R22)R23,
R22 is hydrogen or 1-4C-alkyl,
R23 is hydrogen or 1-4C-alkyl,
or R22 and R23 together and with inclusion of the nitrogen atom to which they are bonded, form a 1-pyrrolidinyl-, 1-piperidinyl-, 1-piperazinyl, 1-(1-4C-alkyl)-piperazin-4-yl-, 1-hexahydroazepinyl-, 4-morpholinyl, 4-thiomorpholinyl-, pyrrolidin-2,5-dione-1-yl-, morpholin-3,5-ione-4-yl-, piperidin-2,6-dione-1-yl, 4,4dimethyl-piperidin-2,6-dione-1-yl or a 1-methyl-imidazolidine-2,4-dione-3-yl-ring or a isoindol-1,3-dione-2-yl-ring-system,
n is an integer from 1 to 4,
m is an integer from 1 to 4,
and the salts of these compounds.

A subgroup of embodiment A to be emphasized are those compounds of formula 1 in which
R1 is methyl or ethyl,
R2 is methyl or ethyl,
R3 represents a phenyl derivative of formulae (a) or (b)

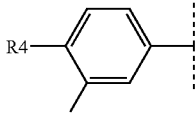

(a)

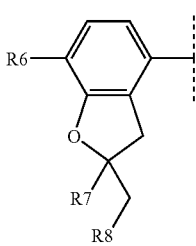

(b)

wherein
R4 is methoxy, ethoxy or difluoromethoxy,
R5 is methoxy, ethoxy or difluoromethoxy,
R6 is methoxy, ethoxy or difluoromethoxy,
R7 is methyl and
R8 is hydrogen,
or wherein
R7 and R8 together and with inclusion of the two carbon atoms, to which they are bonded, form a spiro-linked cyclopentane, cyclohexane, tetrahydrofuran or tetrahydropyran ring,
R9 is —C(O)—R10,
R10 is phenyl or phenyl substituted by R13,
R13 is 1-4C-alkyl or 1-4C-alkoxy,
and the salts of these compounds.

Another subgroup of embodiment A to be emphasized are those compounds of formula 1 in which
R1 is methyl or ethyl,
R2 is methyl or ethyl,
R3 represents a phenyl derivative of formulae (a) or (b)

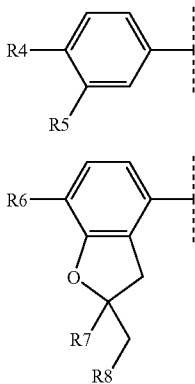

(a)

(b)

wherein
R4 is methoxy, ethoxy or difluoromethoxy,
R5 is methoxy, ethoxy or difluoromethoxy,
R6 is methoxy, ethoxy or difluoromethoxy,
R7 is methyl and
R8 is hydrogen,
or wherein
R7 and R8 together and with inclusion of the two carbon atoms, to which they are bonded, form a spiro-linked cyclopentane, cyclohexane, tetrahydrofuran or tetrahydropyran ring,
R9 is —S(O)$_2$—R14,
R14 is —N(R15)R16, phenyl or phenyl substituted by R17,
R15 is hydrogen or 1-4C-alkyl,
R16 is hydrogen or 1-4C-alkyl,
R17 is halogen, nitro, cyano, 1-4C-alkyl, 1-4C-alkoxy or 1-4C-alkoxy which is completely or predominantly substituted by fluorine,
and the salts of these compounds.

A further subgroup of embodiment A to be emphasized are those compounds of formula 1 in which
R1 is methyl or ethyl,
R2 is methyl or ethyl,
R3 represents a phenyl derivative of formulae (a) or (b)

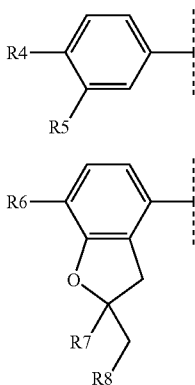

(a)

(b)

wherein
R4 is methoxy, ethoxy or difluoromethoxy,
R5 is methoxy, ethoxy or difluoromethoxy,
R6 is methoxy, ethoxy or difluoromethoxy,
R7 is methyl and
R8 is hydrogen,
or wherein
R7 and R8 together and with inclusion of the two carbon atoms, to which they are bonded, form a spiro-linked cyclopentane, cyclohexane, tetrahydrofuran or tetrahydropyran ring,
R9 is —(CH$_2$)$_n$—C(O)—R18,
R18 is —N(R19)R20,
R19 is hydrogen or 1-4C-alkyl,
R20 is hydrogen or 1-4C-alkyl,
or R19 and R20 together and with inclusion of the nitrogen atom to which they are bonded, form a 1-pyrrolidinyl-, 1-piperidinyl-, 1-piperazinyl, 1-(1-4C-alkyl)-piperazin-4-yl-, 1-hexahydroazepinyl-, 4-morpholinyl or 4-thiomorpholinyl-ring,
n is 1 or 2,
and the salts of these compounds.

Still a further subgroup of embodiment A to be emphasized are those compounds of formula 1 in which
R1 is methyl or ethyl,
R2 is methyl or ethyl,
R3 represents a phenyl derivative of formulae (a) or (b)

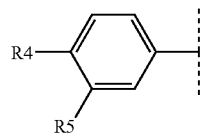

(a)

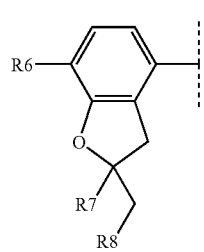

(b)

wherein
R4 is methoxy, ethoxy or difluoromethoxy,
R5 is methoxy, ethoxy or difluoromethoxy,
R6 is methoxy, ethoxy or difluoromethoxy,
R7 is methyl and
R8 is hydrogen,
or wherein
R7 and R8 together and with inclusion of the two carbon atoms, to which they are bonded, form a spiro-linked cyclopentane, cyclohexane, tetrahydrofuran or tetrahydropyran ring,
R9 is —C(O)—(CH$_2$)$_m$—R21,
R21 is —N(R22)R23,
R22 is hydrogen or 1-4C-alkyl,
R23 is hydrogen or 1-4C-alkyl,
or R22 and R23 together and with inclusion of the nitrogen atom to which they are bonded, form a 1-pyrrolidinyl-, 1-piperidinyl-, 1-piperazinyl, 1-methyl-piperazin-4-yl-, 1-hexahydroazepinyl-, 4-morpholinyl-, 4-thiomorpholinyl-, pyrrolidin-2,5dione-1-yl-, morpholin-3,5-dione-4-yl-, piperidin-2,6-dione-1-yl, 4,4-dimethyl-pipe(idin-2,6-dione-1-yl or a 1-methyl-imidazolidine-2,4-dione-3-yl-ring or a isoindol-1,3-dione-2-yl-ring-system,
m is 1,
and the salts of these compounds.

A subgroup of embodiment A to be particularly emphasized are those compounds of formula 1 in which
R1 is methyl or ethyl,
R2 is methyl or ethyl,
R3 represents a phenyl derivative of formulae (a) or (b)

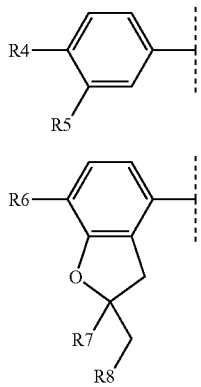

wherein
R4 is methoxy or ethoxy,
R5 is methoxy or ethoxy,
R6 is methoxy,
R7 is methyl and
R8 is hydrogen,
R9 is —C(O)—R10,
R10 is phenyl or phenyl substituted by R13,
R13 is methoxy,
and the salts of these compounds.

Another subgroup of embodiment A to be particularly emphasized are those compounds of formula 1 in which
R1 is methyl or ethyl,
R2 is methyl or ethyl,
R3 represents a phenyl derivative of formulae (a) or (b)

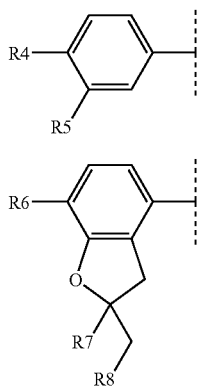

wherein
R4 is methoxy or ethoxy,
R5 is methoxy or ethoxy,
R6 is methoxy,
R7 is methyl and
R8 is hydrogen,
R9 is —S(O)$_2$—R14,
R14 is —N(R15)R16, phenyl or phenyl substituted by R17,
R15 is methyl,
R16 is methyl,
R17 is cyano, methyl, methoxy or trifluoromethoxy,
and the salts of these compounds.

A further subgroup of embodiment A to be particularly emphasized are those compounds of formula 1 in which
R1 is methyl or ethyl,
R2 is methyl or ethyl,
R3 represents a phenyl derivative of formulae (a) or (b)

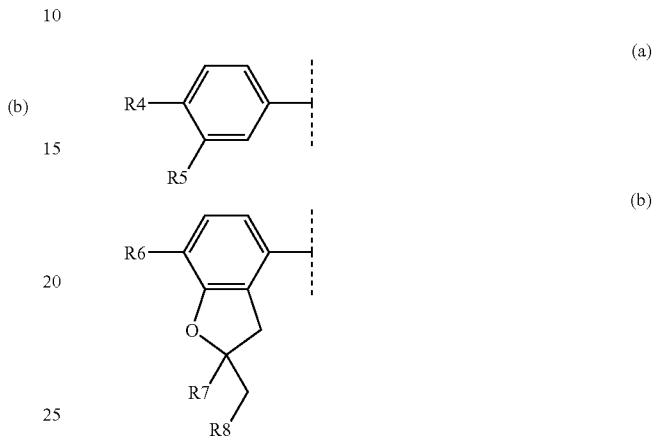

wherein
R4 is methoxy or ethoxy,
R5 is methoxy or ethoxy,
R6 is methoxy,
R7 is methyl and
R8 is hydrogen,
R9 is —(CH$_2$)$_n$—C(O)—R18,
R18 is —N(R19)R20,
R19 is hydrogen,
R20 is hydrogen, or R19 and R20 together and with inclusion of the nitrogen atom to which they are bonded, form a 4-morpholinyl-ring,
n is 1 or 2,
and the salts of these compounds.

Still a further subgroup of embodiment A to be particularly emphasized are those compounds of formula 1 in which
R1 is methyl or ethyl,
R2 is methyl or ethyl,
R3 represents a phenyl derivative of formulae (a) or (b)

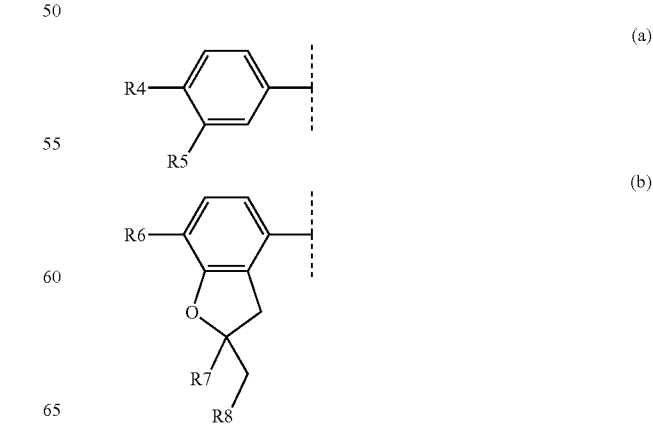

wherein
R4 is methoxy or ethoxy,
R5 is methoxy or ethoxy,
R6 is methoxy,
R7 is methyl and
R8 is hydrogen,
R9 is —C(O)—(CH$_2$)$_m$—R21,
R21 is —N(R22)R23,
or R22 and R23 together and with inclusion of the nitrogen atom to which they are bonded, form a 1-methyl-piperazin4-yl-, pyrrolidin-2,5-dione-1-yl- or a morpholin-3,5-dione-4-yl-ring or a isoindol-1,3-dione-2-yl-ring-system,
m is 1,
and the salts of these compounds.

Another embodiment (embodiment B) of the invention are those compounds of formula 1 in which
R1 is 1-4C-alkyl and
R2 is 1-4C-alkyl,
R3 represents a phenyl derivative of formulae (a) or (b)

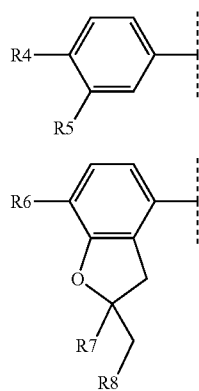

wherein
R4 is 1-4C-alkoxy or 1-4C-alkoxy which is completely or predominantly substituted by fluorine,
R5 is 1-8C-alkoxy, 3-7C-cycloalkoxy, 3-7C-cycloalkylmethoxy, or 1-4C-alkoxy which is completely or predominantly substituted by fluorine,
R6 is 1-4C-alkoxy, 3-5C-cycloalkoxy, 3-5C-cycloalkylmethoxy, or 1-4C-alkoxy which is completely or predominantly substituted by fluorine,
R7 is 1-4C-alkyl and
R8 is hydrogen or 1-4C-alkyl,
or wherein
R7 and R8 together and with inclusion of the two carbon atoms, to which they are bonded, form a spiro-linked 5-, 6- or 7-membered hydrocarbon ring, optionally interrupted by an oxygen or sulphur atom,
R9 is —C(O)R10, —S(O)—R14, —(CH$_2$)$_n$—C(O)—R18 or —C(O)—(CH$_2$)$_m$—R21,
R10 is 1-4C-alkyl, —N(R11)R12, phenyl or phenyl substituted by R13,
R11 is hydrogen, 1-4C-alkyl, 3-7C-cycloalkyl or 3-7C-cycloalkylmethyl,
R12 is hydrogen, 1-4C-alkyl, 3-7C-cycloalkyl or 3-7C-cycloalkylmethyl,
or R11 and R12 together and with inclusion of the nitrogen atom to which they are bonded, form a 1-pyrrolidinyl-, 1-piperidinyl-, 1-piperazinyl, 1-(1-4C-alkyl)-piperazin4-yl-, 1-hexahydroazepinyl-, 4-morpholinyl, 4-thiomorpholinyl-, thiomorpholin-1-oxide-4-yl- or thiomorpholin-1,1-dioxide-4-yl-ring,
R13 is hydroxyl, halogen, nitro, cyano, hydroxycarbonyl, 1-4C-alkyl, trifluoromethyl, 1-4C-alkoxy, 1-4C-alkoxy which is completely or predominantly substituted by fluorine, 1-4C-alkoxycarbonyl, amino, mono- or di-1-4C-alkylamino, aminocarbonyl, mono- or di-1-4C-alkylaminocarbonyl, 1-4C-alkylcarbonyl, 1-4C-alkylcarbonylamino or 1-4C-alkylcarbonyloxy,
R14 is 1-4C-alkyl, —N(R15)R16, phenyl or phenyl substituted by R17,
R15 is hydrogen, 1-4C-alkyl, 3-7C-cycloalkyl or 3-7C-cycloalkylmethyl,
R16 is hydrogen, 1-4C-alkyl, 3-7C-cycloalkyl or 3-7C-cycloalkylmethyl,
or R15 and R16 together and with inclusion of the nitrogen atom to which they are bonded, form a 1-pyrrolidinyl-, 1-piperidinyl-, 1-piperazinyl, 1-(1-4C-alkyl)-piperazin-4-yl-, 1-hexahydroazepinyl-, 4-morpholinyl, 4-thiomorpholinyl-, thiomorpholin-1-oxide-4-yl- or thiomorpholin-1,-dioxide-4-yl-ring,
R17 is hydroxyl, halogen, nitro, cyano, carboxyl, 1-4C-alkyl, trifluoromethyl, 1-4C-alkoxy, 1-4C-alkoxy which is completely or predominantly substituted by fluorine, 1-4C-alkoxycarbonyl, amino, mono- or di-1-4C-alkylamino, aminocarbonyl, mono- or di-1-4C-alkylaminocarbonyl, 1-4C-alkylcarbonyl, 1-4C-alkylcarbonylamino or 1-4C-alkylcarbonyloxy,
R18 is —N(R19)R20,
R19 is hydrogen, 1-4C-alkyl, 3-7C-cycloalkyl or 3-7C-cycloalkylmethyl,
R20 is hydrogen, 1-4C-alkyl, 3-7C-cycloalkyl or 3-7C-cycloalkylmethyl,
or R19 and R20 together and with inclusion of the nitrogen atom to which they are bonded, form a 1-pyrrolidinyl-, 1-piperidinyl-, 1-piperazinyl, 1-(1-4C-alkyl)-piperazin-4-yl-, 1-hexahydroazepinyl-, 4-morpholinyl, 4-thiomorpholinyl-, thiomorpholin-1-oxide-4-yl- or thiomorpholin-1,1-dioxide-4-yl-ring,
R21 is —N(R22)R23,
R22 is hydrogen, 1-4C-alkyl, 3-7C-cycloalkyl or 3-7C-cycloalkylmethyl,
R23 is hydrogen, 1-4C-alkyl, 3-7C-cycloalkyl or 3-7C-cycloalkylmethyl,
or R22 and R23 together and with inclusion of the nitrogen atom to which they are bonded, form a 1-pyrrolidinyl-, 1-piperidinyl-, 1-piperazinyl, 1-(1-4C-alkyl)-piperazin-4-yl-, 1-hexahydroazepinyl-, 4-morpholinyl, 4-thiomorpholinyl-, thiomorpholin-1-oxide-4-yl-, thiomorpholin-1,1-dioxide4-yl- or a pyrrolidin-2,5-dione-1-yl-ring,
n is an integer from 1 to 4,
m is an integer from 1 to 4,
and the salts of these compounds.

Compounds of formula 1 of embodiment B to be emphasized are those in which

R1 is 1-4C-alkyl,
R2 is 1-4C-alkyl,
R3 represents a phenyl derivative of formulae (a) or (b)

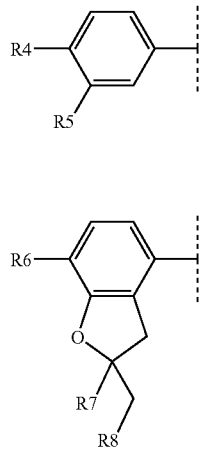

wherein
R4 is 1-2C-alkoxy or 1-2C-alkoxy which is completely or predominantly substituted by fluorine,
R5 is 1-4C-alkoxy,
R6 is 1-2C-alkoxy or 1-2C-alkoxy which is completely or predominantly substituted by fluorine,
R7 is methyl and
R8 is hydrogen,
or wherein
R7 and R8 together and with inclusion of the two carbon atoms, to which they are bonded, form a spiro-linked cyclopentane, cyclohexane, tetrahydrofuran or tetrahydropyran ring,
R9 is —S(O)$_2$—R14, —(CH$_2$)$_n$—(O)—R18 or —C(O)—(CH$_2$)$_m$—R21,
R14 is phenyl or phenyl substituted by R17,
R17 is halogen, nitro, cyano, 1-4C-alkyl or 1-4C-alkoxy,
R18 is —N(R19)R20,
R19 is hydrogen or 1-4C-alkyl,
R20 is hydrogen or 1-4C-alkyl,
or R19 and R20 together and with inclusion of the nitrogen atom to which they are bonded, form a 1-pyrrolidinyl-, 1-piperidinyl-, 1-piperazinyl-, 1-(1-4C-alkyl)-piperazin-4-yl-, 1-hexahydroazepinyl-, 4-morpholinyl or 4-thiomorpholinyl-ring,
R21 is —N(R22)R23,
R22 is hydrogen or 1-4C-alkyl,
R23 is hydrogen or 1-4C-alkyl,
or R22 and R23 together and with inclusion of the nitrogen atom to which they are bonded, form a 1-pyrrolidinyl-, 1-piperidinyl-, 1-piperazinyl-, 1-(1-4C-alkyl)-piperazin-4-yl-, 1-hexahydroazepinyl-, 4-morpholinyl-, 4-thiomorpholinyl- or a pyrrolidin-2,5-dione-1-yl-ring,
n is an integer from 1 to 4,
m is an integer from 1 to 4,
and the salts of these compounds.
Preferred compounds of formula 1 of embodiment B are those, in which R1 is methyl,
R2 is methyl,
R3 represents a phenyl derivative of formula (a)

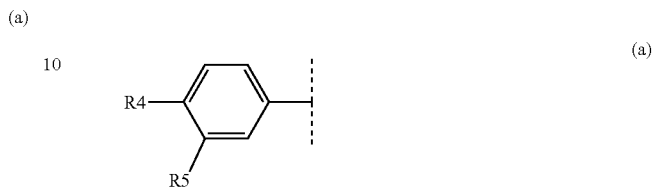

wherein
R4 is methoxy or ethoxy,
R5 is methoxy or ethoxy,
R9 is —S(O)$_2$—R14, —(CH$_2$)$_n$—C(O)—R18 or —C(O)—(CH$_2$)$_m$—R21,
R14 is 2-cyanophenyl,
R18 is amino or 4-morpholinyl,
R21 is pyrrolidin-2,5-dione-1-yl,
n is 1 or 2,
m is 1,
and the salts of these compounds.

A special embodiment of the compounds of the present invention include those compounds of formula 1 in which R3 represents a phenyl derivative of formula (a).

Another special embodiment of the compounds of the present invention include those compounds of formula 1 in which R3 represents a phenyl derivative of formula (a) and R4 and R5 have the meaning methoxy.

Still another special embodiment of the compounds of the present invention include those compounds of formula 1 in which R1 is methyl, R2 is methyl, R3 represents a phenyl derivative of formula (a) and R4 and R5 have the meaning methoxy.

A further special embodiment of the compounds of the present invention include those compounds of formula 1 in which R3 represents a phenyl derivative of formula (b).

Still a further special embodiment of the compounds of the present invention include those compounds of formula 1 in which R1 is methyl, R2 is methyl, R3 represents a phenyl derivative of formula (b), R6 is methoxy, R7 is methyl and R8 is hydrogen.

The compounds of formula 1 are chiral compounds, if the meanings of R1 and R2 are not identical. In case R3 represents a phenyl derivative of formula (b) there is one further chiral center in the dihydrofuran-ring, if the substituents —R7 and —CH$_2$R8 are not identical. However, preferred are in this connection those compounds, in which the substituents —R7 and —CH$_2$R8 are identical or together and with inclusion of the two carbon atoms to which they are bonded form a spiro-connected 5-, 6- or 7-membered hydrocarbon ring.

The invention includes all conceivable pure diastereomers and pure enantiomers of the compounds of formula 1, as well as all mixtures thereof independent from the ratio, including the racemates.

The compounds of formula 1 according to the invention can be prepared, for example, as described in Reaction scheme 1.

Reaction scheme 1:
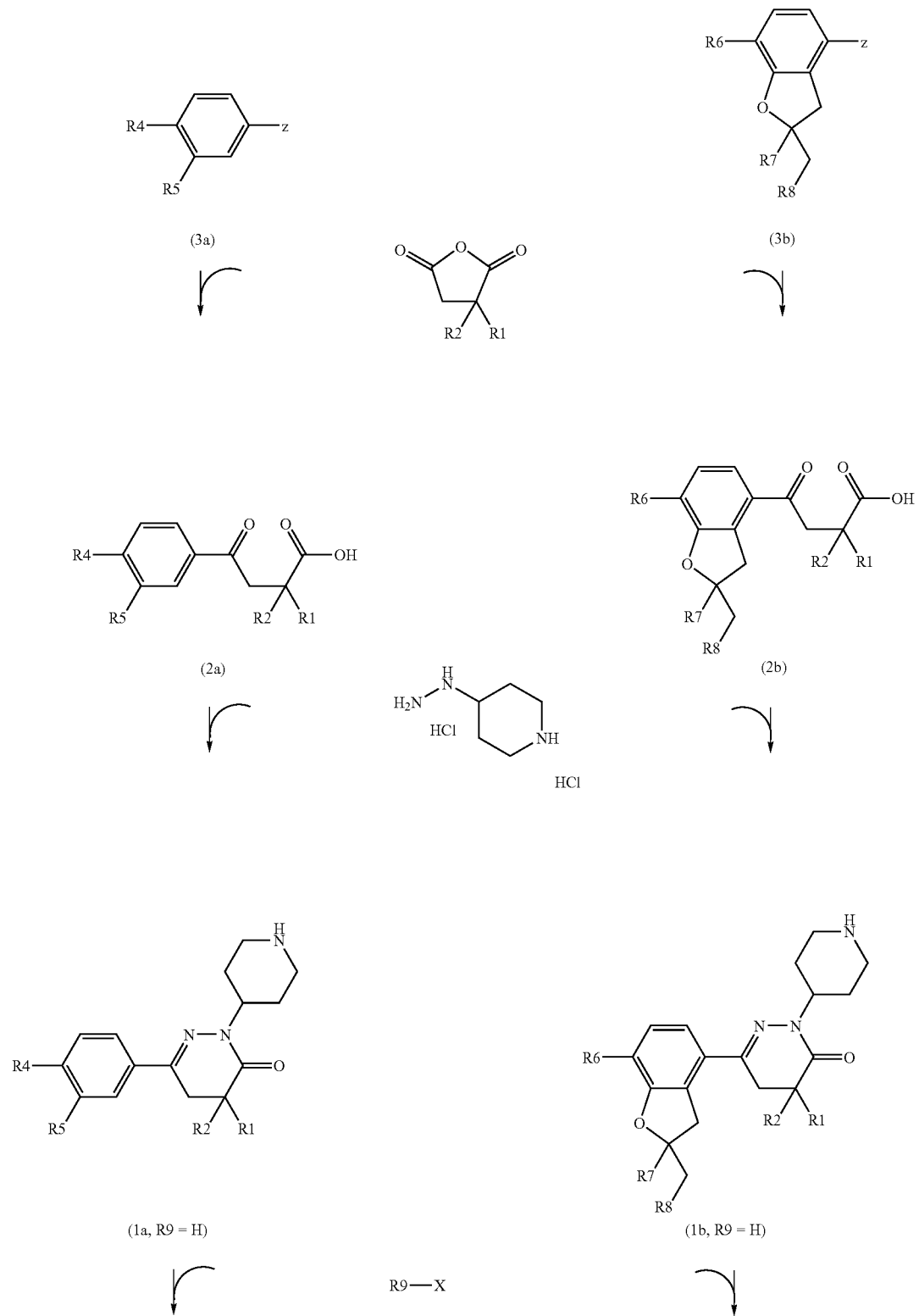

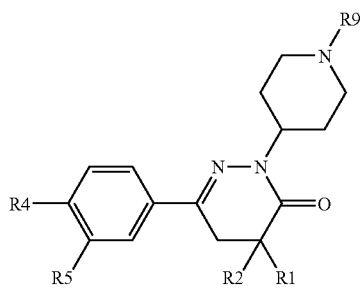

(1a)

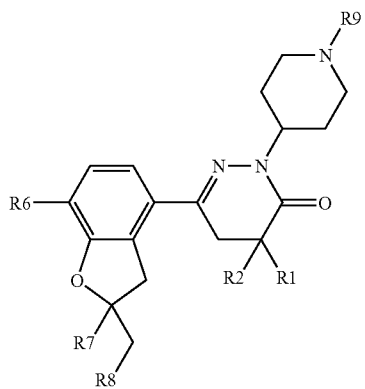

(1b)

In reaction scheme 1, the keto acids of formula 2a, in which R1, R2, R4 and R5 have the above-mentioned meanings, can, for example, be prepared from compounds of formula 3a, in which R4 and R5 have the above-mentioned meanings and Z represents hydrogen (H) by a Friedel-Crafts acylation with 3,3-di-(1-4C-alkyl)-dihydro-furan-2,5-dione (for example 3,3-di-methyl-dihydro-furan-2,5-dione). The Friedel-Crafts acylation is carried out in a manner, which is known to the person skilled in the art (for example as described in M. Yamaguchi et al., J Med Chem 36: 4052-4060, 1993) in presence of a suitable catalyst, such as for example, $AlCl_3$, $ZnCl_2$, $FeCl_3$ or iodine, in an appropriate inert solvent, such as methylene chloride or nitrobenzene or another inert solvent such as diethyl ether, preferably at raised temperature, especially at the boiling point of the solvent being used.

Alternatively, the compounds of formula 2a, in which R1, R2, R4 and R5 have the above-mentioned meanings, can be prepared from compounds of the formula 3a, in which R4 and R5 have the above-mentioned meanings and Z represents a halogen atom through reaction with 3,3-di-(1-4C-alkyl)-dihydro-furan-2,5-dione.

The reaction is carried out in a manner, which is known by a person skilled in the art, for example a) by activating compounds of formula 3a, in which R4, R5 and Z have the above-mentioned meanings, by a lithium/halogen exchange reaction at low temperatures (preferably at −60 to −100° C.) in an appropriate inert solvent such as tetrahydrofuran or diethylether, preferably under an atmosphere of inert gas, followed by reaction of the lithiated compounds with 3,3-di-(1-4C-alkyl)-dihydro-furan-2,5-dione, or b) by converting compounds of formula 3a, in which R4, R5 and Z have the above-mentioned meanings, in a suitable inert solvent such as, for example, tetrahydrofuran or diethyl ether into the corresponding Grignard compounds of formula 3a, in which Z represents MgCl, MgBr or MgI followed by reaction of the Grignard compounds with 3,3-di-(1-4C-alkyl)-dihydro-furan-2,5-dione.

Compounds of formula 2b, in which R1, R2, R6, R7 and R8 have the above-mentioned meanings can be prepared analogously to the compounds of formula 2a using the synthesis procedures described above under a) or b).

Compounds of formula 3a, in which R4 and R5 have the above-mentioned meanings and Z represents a hydrogen (H) or halogen atom, are known or can be prepared as described in WO98/31674.

Compounds of formula 3b, in which R6, R7 and R8 have the above-mentioned meanings and Z represents a halogen atom, are known or can be prepared as described in WO99/31090.

The keto acids of formulae 2a and 2b are converted to compounds of formula 1 a and 1 b, in which R1, R2, R4, R5, R6, R7 and R8 have the above-mentioned meanings and R9 represents hydrogen (H) by a reaction with 4-hydrazinopiperidine dihydrochloride.

The conversion of the keto acids of formulae 2a and 2b or one of their reactive derivatives with 4-hydrazinopiperidine dihydrochloride is advantageously carried out with 1 to 1.5 equivalents of the 4-hydrazinopiperidine dihydrochloride in the presence of a suitable base, such as for example, triethylamine, diisopropylethylamine, N-methylmorpholine or any other aliphatic tertiary amine. As inert solvents are preferably used alcohols such as methanol, ethanol, isopropanol, n-propanol, n-butanol, isoamylalcohol, glycols and their ethers such as ethylene glycol, diethylene glycol, ethylene glycol monomethyl or monoethyl ether, acids such as formic acid, acetic or propionic acid, suitable mixtures of the above-mentioned solvents, as well as mixtures with water, for example aqueous ethanol, further ethers, especially water soluble ethers such as tetrahydrofuran, dioxane or ethylene glycol dimethylether; further toluene or benzene, especially when the method of azeotropic destillation is used to remove the reaction water.

The reaction temperatures are suitably between 0 and 200° C., preferably between 20 and 100° C.; the reaction times are preferably between 1 and 48 hours.

Suitable reactive derivatives of the keto acids of formulae 2a and 2b which may be mentioned in this context are, for example, esters, especially methyl and ethyl esters, nitrils and acid halides, such as acid chlorides or acid bromides. They can be prepared by methods, which are known by the person skilled in the art.

Finally, the compounds of formulae 1a and 1b, in which R1, R2, R4, R5, R6, R7 and R8 have the above-mentioned meanings and R9 has the meaning hydrogen (H) are reacted with a compound of formula R9-X in which R9 has the above-mentioned meanings and X is a suitable leaving group, for example a halogen atom, preferably a chlorine atom.

All known classical methods for alkylation, reaction with sulfonyl halides, reaction with acyl halides etc. can be used in this last reaction step.

Alternatively, in some cases, it might be useful to introduce the substituent R9 by a Michael addition reaction or by a two- or multi-step procedure.

Suitably, the conversions are carried out analogous to methods, which are familiar per se to the person skilled in the art, for example, in the manner which is described in the following examples.

The substances according to the invention are isolated and purified in a manner known per se, e.g. by distilling off the solvent in vacuo and recrystallising the residue obtained from a suitable solvent or subjecting it to one of the customary purification methods, such as column chromatography on a suitable support material.

Salts are obtained by dissolving the free compound in a suitable solvent (for example a ketone like acetone, methylethylketone, or methylisobutylketone, an ether, like diethyl ether, tetrahydrofuran or dioxane, a chlorinated hydrocarbon, such as methylene chloride or chloroform, or a low molecular weight aliphatic alcohol, such as ethanol, isopropanol) which contains the desired acid, or to which the desired acid is then added. The salts are obtained by filtering, reprecipitating, precipitating with a non-solvent for the addition salt or by evaporating the solvent. Salts obtained can be converted by basification into the free compounds which, in turn, can be converted into salts. In this manner, pharmacologically non-tolerable salts can be converted into pharmacologically tolerable salts.

The following examples illustrate the invention in greater detail, without restricting it. As well, further compounds of formula 1, of which the preparation is explicitly not described, can be prepared in an analogous way or in a way which is known by a person skilled in the art using customary preparation methods.

The compounds, which are mentioned in the examples as well as their salts are preferred compounds of the invention. In the examples, RT stands for room temperature, h for hour(s), min for minute(s) and M. p. for melting point.

EXAMPLES

Final Products 1. 2-{4-[3-(3,4-dimethoxy-phenyl)-5.5-dimethyl-6-oxa-5,6-dihydro-4H-pyridazin-1-yl]-piperidine-1-sulfonyl}-benzonitrile A mixture of 5 mmol of intermediate A2, 7 mmol of 2-cyanobenzenesulfonyl chloride and 10 mmol of triethylamine in 50 ml of dichloromethane is stirred at RT for 1 h. The organic layer is washed twice with aqueous sodium carbonate, dried over $MgSO_4$ and concentrated in vacuo. The title compound crystallizes from ethyl acetate. M. p. 190-192° C.

2. 6-(3.4Dimethoxy-phenyl)-4,4dimethyl-2-[1-(3-morpholin-4-yl-3-oxo-propyl)piperidin-4-yl]-4,5-dihydro-2H-pyridazin-3-one hydrochloride A solution of 5 mmol of intermediate A2 and 8 mmol of 1-morpholin-4-yl-propenone in 50 ml of methanol is stirred for 20 h at RT. After evaporating the residue is dissolved in ethyl acetate and filtered. A saturated solution of hydrochloric acid in diethyl ether is added and the resulting precipitate is filtered off and dried. M. p. 211-213° C.

3. 2-[4-(3-{3,4dimethoxyphenyl}-6-oxa-5,6-dihydro-4H-pyridazin-1-yl)-piperidin-1-yl]-acetamide A mixture of 5 mmol of intermediate A2, 15 mmol of potassium carbonate and 7 mmol of chloroacetamide in 10 ml of dimethyl formamide is stirred for 72 h at RT. The solvent is evaporated and the residue is partitioned between aqueous sodium carbonate and ethyl acetate. The organic layer is dried over $MgSO_4$ and concentrated in vacuo. The product is purified by chromatography (ethyl acetate:methanol/10:1) and crystallized from ethyl acetate. M. p. 180-182° C.

4. 1-2-{4-[3-(3,4Dimethoxy-phenyl)-5,5-dimethyl-6-oxo-5,6-dihydro-4H-pyridazin-1-yl]-piperidin-1-yl}-2-oxo-ethyl)-pyrrolidine-2,5-dione 10 mmol of chloroacetyl chloride, dissolved in 20 ml of dichloromethane is added slowly to a solution of 5 mmol of intermediate A2 and 20 mmol of triethylamine in 50 ml of dichloromethane at 0° C. After complete addition the mixture is stirred for an additional 30 min after which 50 ml of water is added and stirring is continued for additional 30 min. The dichloromethane solution is separated, washed twice with water, dried over magnesium sulfate and evaporated. The residue is dissolved in ethyl acetate, filtered over silica gel after which the solvent is evaporated. The residue is dissolved in 20 ml of dimethyl formamide and 10 mmol of succinimide and 10 mmol of potassium carbonate are added and the resulting mixture is heated for 2 h at 70° C. After cooling to RT, the mixture is diluted with 100 ml of ethyl acetate and filtered. After evaporating the solvent, the residue is purified by chromatography (elution with ethyl acetate:methanol/5:1). Crystallisation from ethyl acetate yields the title compound. M. p. 177-179° C.

5. 6-(3,4Dimethoxy-phenyl)4,4dimethyl-2-[1-(toluene-2-sulfanyl)-peridin-4-yl]-4.5-dihydro-2H-pyridazin-3-one The title compound is prepared analogous as described for Example 1 using intermediate A2 and 2-methyl-benzenesulfonyl chloride. M. p. 132-133° C.

6. 4-{4-[3-(3,4-Dimethoxy-phenyl)-5,5-dimethyl-6-oxo-5,6-dihydro-4H-pyridazin-1-yl]-piperidine-1-sulfonyl}-benzonitrile The title compound is prepared analogous as described for Example 1 using intermediate A2 and 4-cyano-benzenesulfonyl chloride. M. p. 161-163° C.

7. 6-(3,4-Dimethoxy-phenyl)-4,4-dimethyl-2-[1-(2-trifluoromethoxy-benzenesulfonyl)-piperidin-4-yl]-4,5-dihydra-2H-pyridazin-3-one The title compound is prepared analogous as described for Example 1 using intermediate A2 and 2-trifluoromethyl-benzenesulfonyl chloride. M. p. 143-144° C.

8. 6-(3,4Dimethoxy-phenyl)-2-{1-[1-(2-methoxy-phenyl)methanoyl]-piperidin-4-yl}-4,4-dimethyl-4,5-dihydro-2H-pyridazin-3-one The title compound is prepared analogous as described for Example 1 using intermediate A2 and 2-methoxy-benzoyl chloride. M. p. 157-159° C.

9. 3-{4-[3-(3,4-Dimethoxy-phenyl)-5,-dimethyl-6-oxo-5,6-dihydro-4H-pyridazin-1-yl]-piperidine-1-sulfonyl}-benzonitrile The title compound is prepared analogous as described for Example 1 using intermediate A2 and 3-cyano-benzenesulfonyl chloride. M. p. 158-160° C.

10. 6-(3,4Dimethoxy-phenyl)-4,4-dimethyl-2-[1-(toluene-4-sulfonyl)-piperidin-4-yl]-4,5-dihydro-2H-pyridazin-3-one The title compound is prepared analogous as described for Example 1 using intermediate A2 and 4-methyl-benzene-sulfonyl chloride. M. p. 161-164° C.

11. 6-(3,4Dimethoxy-phenyl)-4,4-dimethyl-2-[1-(toluene-3-sulfonyl)-piperidin-4-yl]-4,5-dihydro-2H-pyridazin-3-one The title compound is prepared analogous as described for Example 1 using intermediate A2 and 3-methyl-benzene-sulfonyl chloride. M. p. 150-152° C.

12. 4-[3-(3,4-Dimethoxy-phenyl)-5,5dimethyl-6-oxo-5,6-dihydro-4H-pyridazin-1-yl]-piperidine-1-sulfonic acid dimethylamide The title compound is prepared analogous as described for Example 1 using intermediate A2 and dimethylsulfamoyl-chloride. M. p. 172-174° C.

13. 2-{4-[3-(7-Methoxy-2,2-dimethyl-2,3-dihydro-benzofuran-4-yl)-5,5-dimethyl-6-oxo-5,6-dihydro-4H-pyridazin-1-yl]-piperidin-1-yl}-acetamide The title compound is prepared analogous as described for Example 3 using intermediate A4 and 2-chloroacetamide. M. p. 215-216° C.

14. 6-(3,4-Dimethoxy-phenyl)-4,4-diethyl-2-[1-(1-phenyl-methanoyl)-piperidin-4-yl]-4,5-dihydro-2H-pyridazin-3-one The title compound is prepared analogous as described for Example 1 using intermediate A6 and benzoyl chloride. M. p. 160-61° C.

15. 2-{4-[3-(3,4Dimethoxy-phenyl)-5,5-diethyl-6-oxo-5,6-dihydro-4H-pyridazin-1-yl]-piperidin-1-yl}-cetamide hydrochloride The title compound is prepared analogous as described for Example 3 using intermediate A6 and 2-chloroacetamide. M. p. 69-74° C.

16. 2-{4-[3-(3,4Dimethoxy-phenyl)-5,5-diethyl-6-oxo-5,6-dihydro-4-pyridazin-1-yl]-piperidine-1-sulfonyl}-benzonitrile The title compound is prepared analogous as described for Example 1 using intermediate A6 and 2-cyano-benzenesulfonyl chloride. M. p. 156-157° C.

17. 4-(2-{4-[3-(3,4-Dimethoxy-phenyl)-5,5-dimethyl-6-oxo-5,6-dihydro-4H-pyridazin-1-yl]-piperidin-1-yl}-2-oxo-ethyl)-mornholine-3,5-dione The title compound is prepared analogous as described for Example 4 using intermediate A2 and morpholine-3,5-dione. M. p. 210-211° C.

18. 6-(3,4-Dimethoxy-phenyl)-4,4-diethyl-2-{1-[1-(2-methoxy-phenyl)-methanoyl]-piperidin-4-yl}-4,5-dihydro-2H-pyridazin-3-one The title compound is prepared analogous as described for Example 1 using intermediate A6 and 2-methoxybenzoyl chloride. M. p. 160-162° C.

19. 6-(7-Methoxy-2,2-dimethyl-2,3-dihydro-benzofuran-4-yl)-4,4-dimethyl-2-{1-[2-(4-methyl-piperazin-1-yl)-ethanoyl]-piperidin-4-yl}-4,5-dihydro-2H-pyridazin-3-one The title compound is prepared analogous as described for Example 4 using intermediate A4 and N-methylpiperazine. M. p. 121-123° C.

20. 1-(2-{4-[3-(7-Methoxy-2,2-dimethyl-2,3-dihydro-benzoluran-4-yl)-5,5-dimethyl-6-oxo-5,6-dihydro-4H-pyridazin-1-yl]-piperidin-1-yl}-2-oxo-ethyl)-pyrrolidine-2,5-dione The title compound is prepared analogous as described for Example 4 using intermediate A6 and pyrrolidine-2,5-dione. M. p. 240-241° C.

21. 2-(2-{4-[3-(3,4-Dimethoxy-phenyl)-5,5-dimethyl-6-oxo-5,6-dihydro-4H-pyridazin-1-yl]-piperidin-1-yl}-2-oxo-ethyl)-isoindole-1,3-dione The title compound is prepared analogous as described for Example 4 using intermediate A2 and phthalimide. M. p. 193-194° C.

Starting Compounds and Intermediates

A1. 4-(3,4-dimethoxyphenyl)-2,2-dimethyl-4-oxo-butyric acid

Under an atmosphere of dry nitrogen a grignard solution, prepared from 43.4 g 3,4-dimethoxybromobenzene and 6.1 g magnesium in 200 ml of tetrahydrofuran, is added dropwise to a solution of 20.5 g 3,3-dimethyl-dihydro-furan-2,5-dione in 200 ml of tetrahydrofuran cooled in an ice-bath. The reaction mixture is stirred for an additional hour at RT. 100 ml of a 20% ammonium chloride solution is added and the water layer is extracted twice with 75 ml of ethyl acetate. The combined organic layers are washed twice with 100 ml of half saturated brine and extracted with 3×100 ml 1 M sodium hydroxide solution. The aqueous layers are washed with 75 ml of ethyl acetate, acidified with concentrated hydrochloric acid and extracted 3 times with 100 ml of dichloromethane. The organic layers are dried over magnesium sulfate, filtered and concentrated in vacuo. The oily residue is crystallized from ethyl acetate/petroleum ether (60-80° C.). M. p. 114-116° C.

A2. 6-(3,4-dimethoxyphenyl)-4,4dimethyl-2-piperidin-4-yl-4,5-dihydro-2H-pyridazin-3-one A mixture of 50 mmol of intermediate A1, 50 mmol of 4-hydrazinopiperidine dihydrochloride and 15 ml of triethylamine in 100 ml of n-propanol are heated under reflux for 48 h. The solvent is evaporated and the residue is suspended in 100 ml of a 1 M solution of sodium hydroxide. This suspension is extracted 3 times with 50 ml of dichloromethane. The combined organic layers are washed with 50 ml of a 1 M solution of sodium hydroxide, dried over magnesium sulfate, filtered and concentrated in vacuo. Crystallisation from diethyl ether yields the title compound. M. p. 126-128° C.

A3. 4-(7-Methoxy-2,2-dimethyl-2,3-dihydro-benzofuran-4-yl)-2,2-dimethyl-4-oxo-butyric acid The tile compound is prepared analogous as described for intermediate A1 using 4Bromo-7-methoxy-2,2-dimethyl-2,3-dihydro-benzofuran. Crystallised from diethyl ether. M. p. 159-160° C.

A4. 6-(7-Methoxy-2,2-dimethyl-2,3-dihydro-benzofuran-4-yl)-4,4-dimethyl-2-piperldin-4-yl-4,5-dihydro-2H-pridazin-3-one hydrochloride The title compound is prepared analogous as described for intermediate A2 using intermediate A3 and piperidin-4-yl-hydrazine dihydrochloride. M. p.>300° C.

A5. 4-(3,4-Dimethoxy-phenyl)-2,2-diethyl-4-oxo-butyric acid

The title compound is prepared analogous as described for intermediate A1 using 3,3-diethyl-dihydro-furan-2,5-dione. M. p. 106-109° C.

A6. 6-(3,4Dimethoxy-phenyl)-4,4-diethyl-2-piperidin-4-yl-4,5-dihydro-2H-pyridazin-3-one hydrochloride The title compound is prepared analogous as described for intermediate A2 using intermediate A5 and piperidin-4-yl-hydrazine dihydrochloride. M. p. 137-138° C.

Commercial Utility

The compounds according to the invention have useful pharmacological properties which make them industrially utilizable. As selective cyclic nucleofide phosphodiesterase (PDE) inhibitors (specifically of type 4), they are suitable on the one hand as bronchial therapeutics (for the treatment of airway obstructions on account of their dilating action but also on account of their respiratory rate- or respiratory drive-increasing action) and for the removal of erectile dysfunction on account of their vascular dilating action, but on the other hand especially for the treatment of disorders, in particular of an inflammatory nature, e.g. of the airways (asthma prophylaxis), of the skin, of the intestine, of the eyes, of the CNS and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen free radicals and proteases. In this context, the compounds according to the invention are distinguished by a low toxicity, a good enteral absorption (high bioavailability), a large therapeutic breadth and the absence of significant side effects.

On account of their PDE-inhibiting properties, the compounds according to the invention can be employed in human and veterinary medicine as therapeutics, where they can be used, for example, for the treatment and prophylaxis of the following illnesses: acute and chronic (in particular inflammatory and allergen-induced) airway disorders of varying origin (bronchitis, allergic bronchitis, bronchial asthma, emphysema, COPD); dermatoses (especially of proliferative, inflammatory and allergic type) such as psoriasis (vulgaris), toxic and allergic contact eczema, atopic eczema, seborrhoeic eczema, Lichen simplex, sunburn, pruritus in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on an excessive release of TNF and leukotrienes, for example disorders of the arthritis type (rheumatoid arthritis, rheumatoid spondylitis, osteoarthritis and other arthritic conditions), disorders of the immune system (AIDS, multiple sclerosis), graft versus host reaction, allograft rejections, types of shock (septic shock, endotoxin shock, gram-negative sepsis, toxic shock syndrome and ARDS (adult respiratory distress syndrome)) and also generalized inflammations in the gastrointestinal region (Crohn's disease and ulcerative colitis); disorders which are based on allergic and/or chronic, immunological false reactions in the region of the upper airways (pharynx, nose) and the adjacent regions (paranasal sinuses, eyes), such as allergic rhinitis/sinusitis, chronic rhinitis/sinusitis, allergic conjunctivitis and also nasal polyps; but also disorders of the heart which can be treated by PDE inhibitors, such as cardiac insufficiency, or disorders which can be treated on account of the tissue-relaxant action of the PDE inhibitors, such as, for example, erectile dysfunction or colics of the kidneys and of the ureters in connection with kidney stones. In addition, the compounds of the invention are useful in the treatment of diabetes insipidus, diabetes mellitus, leukaemia, osteoporosis and conditions associated with cerebral metabolic inhibition, such as cerebral senility, senile dementia (Alzheimer's disease), memory impairment associated with Parkinson's disease or multiinfarct dementia; and also illnesses of the central nervous system, such as depressions or arteriosclerotic dementia.

The invention further relates to a method for the treatment of mammals, including humans, which are suffering from one of the above mentioned illnesses. The method is characterized in that a therapeutically active and pharmacologically effective and tolerable amount of one or more of the compounds according to the invention is administered to the ill mammal.

The invention further relates to the compounds according to the invention for use in the treatment and/or prophylaxis of illnesses, especially the illnesses mentioned.

The invention also relates to the use of the compounds according to the invention for the production of pharmaceutical compositions which are employed for the treatment and/or prophylaxis of the illnesses mentioned.

The invention furthermore relates to pharmaceutical compositions for the treatment and/or prophylaxis of the illnesses mentioned, which contain one or more of the compounds according to the invention.

Additionally, the invention relates to an article of manufacture, which comprises packaging material and a pharmaceutical agent contained within said packaging material, wherein the pharmaceutical agent is therapeutically effective for antagonizing the effects of the cyclic nucleotide phosphodiesterase of type 4 (PDE4), ameliorating the symptoms of an PDE4-mediated disorder, and wherein the packaging material comprises a label or package insert which indicates that the pharmaceutical agent is useful for preventing or treating PDE4-mediated disorders, and wherein said pharmaceutical agent comprises one or more compounds of formula 1 according to the invention. The packaging material, label and package insert otherwise parallel or resemble what is generally regarded as standard packaging material, labels and package inserts for pharmaceuticals having related utilities.

The pharmaceutical compositions are prepared by processes which are known per se and familiar to the person skilled in the art. As pharmaceutical compositions, the compounds according to the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries or excipients which are suitable for the desired pharmaceutical formulations on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

The administration of the pharmaceutical compositions according to the invention may be performed in any of the generally accepted modes of administration available in the art. Illustrative examples of suitable modes of administration include intravenous, oral, nasal, parenteral, topical, transdermal and rectal delivery. Oral delivery is preferred.

For the treatment of disorders of the respiratory tract, the compounds according to the invention are preferably also administered by inhalation in the form of an aerosol; the aerosol particles of solid, liquid or mixed composition preferably having a diameter of 0.5 to 10 µm, advantageously of 2 to 6 µm.

Aerosol generation can be carried out, for example, by pressure-driven jet atomizers or ultrasonic atomizers, but advantageously by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

For the treatment of dermatoses, the compounds according to the invention are in particular administered in the form of those pharmaceutical compositions which are suitable for topical application. For the production of the pharmaceutical compositions, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the active compounds is carried out in the order of magnitude customary for PDE inhibitors. Topical application forms (such as ointments) for the treatment of dermatoses thus contain the active compounds in a concentration of, for example, 0.1-99%. The dose for administration by inhalation is customarly between 0.1 and 3 mg per day. The customary dose in the case of systemic therapy (p.o. or i.v.) is between 0.03 and 3 mg/kg per day.

Biological Investigations

The second messenger cyclic AMP (cAMP) is well-known for inhibiting inflammatory and immunocompetent cells. The PDE4 isoenzyme is broadly expressed in cells involved in the initiation and propagation of inflammatory diseases (H Tenor and C Schudt, in "Phosphodiesterase Inhibitors", 21-40, "The Handbook of Immunopharmacology", Academic Press, 1996), and its inhibition leads to an increase of the intracellular cAMP concentration and thus to the inhibition of cellular activation (J E Souness et al., Immunopharmacology 47: 127-162, 2000).

The antiinflammatory potential of PDE4 inhibitors in vivo in various animal models has been described (M M Teixeira, TiPS 18: 164-170, 1997). For the investigation of PDE4 inhibition on the cellular level (in vitro), a large variety of proinflammatory responses can be measured. Examples are the superoxide production of neutrophilic (C Schudt et al., Arch Pharmacol 344: 682-690, 1991) or eosinophilic (A Hatzelmann et al., Brit J Pharmacol 114: 821-831, 1995) granulocytes, which can be measured as luminol-enhanced chemiluminescence, or the synthesis of tumor necrosis factor-$\alpha$ in monocytes, macrophages or dendritic cells (Gantner et al., Brit J Pharmacol 121: 221-231, 1997, and Pulmonary Pharmacol Therap 12: 377-386, 1999). In addition, the immunomodulatory potential of PDE4 inhibitors is evident from the inhibition of T-cell responses like cytokine synthesis or proliferation (D M Essayan, Biochem Pharmacol 57: 965-973, 1999). Substances which inhibit the secretion of the aforementioned proinflammatory mediators are those which inhibit PDE4. PDE4 inhibition by the compounds according to the invention is thus a central indicator for the suppression of inflammatory processes.

Method for Measuring Inhibition of PDE4 Activity

PDE4B2 (GB no. M97515) was a gift of Prof. M. Conti (Stanford University, USA). It was amplified from the original plasmid (pCMV5) via PCR with primers Rb9 (5'-GCCAGCGTGCAAATAATGAAGG-3') and Rb10 (5'-AGAGGGGGATTATGTATCCAC-3') and cloned into the pCR-Bac vector (Invitrogen, Groningen, NL).

The recombinant baculovirus was prepared by means of homologous recombination in SF9 insect cells. The expression plasmids were cotransfected with Bac-N-Blue (Invitrogen, Groningen, NL) or Baculo-Gold DNA (Pharmingen, Hamburg) using a standard protocol (Pharmingen, Hamburg). Wt virus-free recombinant virus supernatants were selected using plaque assay methods. After that, high-titre virus supernatants were prepared by amplifying 3 times. PDE4B2 was expressed in SF21 cells by infecting $2 \times 10^6$ cells/ml with an MOI (mulfiplicity of infection) between 1 and 10 in serum-free SF900 medium (Life Technologies, Paisley, UK). The cells were cultured at 28° C. for 48-72 hours, after which they were pelleted for 5-10 min at 1000 g and 40° C.

The SF21 insect cells were resuspended, at a concentration of approx. $10^7$ cells/ml, in ice-cold (4° C.) homogenization buffer (20 mM Tris, pH 8.2, containing the following additions: 140 mM NaCl, 3.8 mM KCl, 1 mM EGTA, 1 mM $MgCl_2$, 10 mM β-mercaptoethanol, 2 mM benzamidine, 0.4 mM Pefablock, 10 μM leupeptin, 10 μM pepstatin A, 5,μM trypsin inhibitor) and disrupted by ultrasonication. The homogenate was then centrifuged for 10 min at 1000×g and the supernatant was stored at −80° C. until subsequent use (see below). The protein content was determined by the Bradford method (BioRad, Munich) using BSA as the standard.

PDE4B2 activity was inhibited by the compounds according to the invention in a modified SPA (scintillation proximity assay) test, supplied by Amersham Biosciences (see procedural instructions "phosphodiesterase [3H]cAMP SPA enzyme assay, code TRKQ 7090"), carried out in 96-well microtitre plates (MTP's). The test volume is 100 μl and contains 20 mM Tris buffer (pH 7.4), 0.1 mg of BSA (bovine serum albumin)/ml, 5 mM $Mg^{2+}$, 0.5 μM cAMP (including about 50,000 cpm of [3H]cAMP), 1 μl of the respective substance dilution in DMSO and sufficient recombinant PDE (1000×g supernatant, see above) to ensure that 10-20% of the cAMP is converted under the said experimental conditions. The final concentration of DMSO in the assays (1% v/v) does not substantially affect the activity of the PDEs investigated. After a preincubation of 5 min at 37° C., the reaction is started by adding the substrate (cAMP) and the assays are incubated for a further 15 min; after that, they are stopped by adding SPA beads (50 μl). In accordance with the manufacturer's instructions, the SPA beads had previously been resuspended in water, but were then diluted 1:3 (v/v) in water; the diluted solution also contains 3 mM IBMX to ensure a complete PDE activity stop. After the beads have been sedimented (>30 min), the MTP's are analyzed in commercially available luminescence detection devices. The corresponding $IC_{50}$ values of the compounds for the inhibition of PDE4B2 activity are determined from the concentration-effect curves by means of non-linear regression.

The inhibitory values determined for the compounds according to the invention follow from the following Table 1, which the numbers of the compounds correspond to the numbers of the examples.

TABLE 1

| Inhibition of PDE4 acitivity [measured as $-logIC_{50}$ (mol/l)] | |
|---|---|
| Compound | PDE4 Inhibition |
| 1 | 9.53 |
| 2 | 7.60 |
| 3 | 8.73 |
| 4 | 8.89 |
| 5 | 9.13 |
| 7 | 8.64 |
| 8 | 9.68 |
| 13 | 9.38 |

TABLE 1-continued

| Inhibition of PDE4 acitivity [measured as $-logIC_{50}$ (mol/l)] | |
|---|---|
| Compound | PDE4 Inhibition |
| 15 | 8.21 |
| 16 | 9.45 |
| 17 | 9.19 |

The invention claimed is:
1. A compound of formula 1

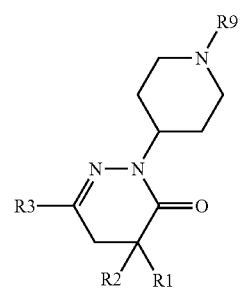

(1)

in which
R1 is 1-4C-alkyl and
R2 is 1-4C-alkyl,
R3 represents a phenyl derivative of formulae (a)

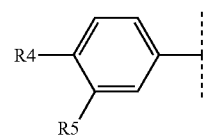

(a)

wherein
R4 is 1-4C-alkoxy or 1-4C-alkoxy which is completely or predominantly substituted by fluorine,
R5 is 1-8C-alkoxy, 3-7C-cycloalkoxy, 3-7C-cycloalkylmethoxy, or 1-4C-alkoxy which is completely or predominantly substituted by fluorine,
R9 is —C(O)R10, —S(O)$_2$—R14, —(CH$_2$)$_n$—C(O)—R18 or —C(O)—(CH$_2$)$_m$—R21,
R10 is 1-4C-alkyl, —N(R11)R12, phenyl or phenyl substituted by R13,
R11 is hydrogen, 1-4C-alkyl, 3-7C-cycloalkyl or 3-7C-cycloalkylmethyl,
R12 is hydrogen, 1-4C-alkyl, 3-7C-cycloalkyl or 3-7C-cycloalkylmethyl,
or R11 and R12 together and with inclusion of the nitrogen atom to which they are bonded, form a 1-pyrrohidinyl-, 1-piperidinyl-, 1-piperazinyl, 1-(1-4C-alkyl)-piperazin-4-yl-, 1-hexahydroazepinyl-, 4-morphohinyl-, 4-thiomorphohinyl-, thiomorphohin-1-oxide-4-yl- or thiomorpholin-1,1-dioxide-4-yl-ring,
R13 is hydroxyl, halogen, nitro, cyano, hydroxycarbonyl, 1-4C-alkyl, trifluoromethyl, 1-4C-alkoxy, 1-4C-alkoxy which is completely or predominantly substituted by fluorine, 1-4C-alkoxycarbonyl, amino, mono- or di-1-4C-alkylamino, aminocarbonyl, mono- or di-1-4C-alkylaminocarbonyl, 1-4C-alkylcarbonyl, 1-4C-alkylcarbonylamino or 1-4C-alkylcarbonyloxy, R14 is 1-4C-alkyl, —N(R15)R16, phenyl or phenyl substituted by R17,
R15 is hydrogen, 1-4C-alkyl, 3-7C-cycloalkyl or 3-7C-cycloalkylmethyl,
R16 is hydrogen, 1-4C-alkyl, 3-7C-cycloalkyl or 3-7C-cycloalkylmethyl,
or R15 and R16 together and with inclusion of the nitrogen atom to which they are bonded, form a 1-pyrrolidinyl-, 1-piperidinyl-, 1-piperazinyl, 1-(1-4C-alkyl)-piperazin-4-yl-, 1-hexahydroazepinyl-, 4-morpholinyl, 4-thiomorpholinyl-, thiomorpholin-1-oxide-4-yl- or thiomorpholin-1,1-dioxide-4-yl-ring,
R17 is hydroxyl, halogen, nitro, cyano, carboxyl, 1-4C-alkyl, trifluoromethyl, 1-4C-alkoxy, 1-4C-alkoxy which is completely or predominantly substituted by fluorine, 1-4C-alkoxycarbonyl, amino, mono- or di-1-4C-alkylamino, aminocarbonyl, mono- or di-1-4C-alkylaminocarbonyl, 1-4C-alkylcarbonyl, 1-4C-alkylcarbonylamino or 1-4C-alkylcarbonyloxy,
R18 is —N(R19)R20,
R19 is hydrogen, 1-4C-alkyl, 3-7C-cycloalkyl or 3-7C-cycloalkylmethyl,
R20 is hydrogen, 1-4C-alkyl, 3-7C-cycloalkyl or 3-7C-cycloalkylmethyl,
or R19 and R20 together and with inclusion of the nitrogen atom to which they are bonded, form a 1-pyrrolidinyl-, 1-piperidinyl-, 1-piperazinyl, 1-(1-4C-alkyl)-piperazin-4-yl-, 1-hexahydroazepinyl-, 4-morpholinyl, 4-thiomorpholinyl-, thiomorpholin-1-oxide-4-yl- or thiomorpholin-1,1-dioxide-4-yl-ring,
R21 is —N(R22)R23,
R22 is hydrogen, 1-4C-alkyl, 3-7C-cycloalkyl or 3-7C-cycloalkylmethyl,
R23 is hydrogen, 1-4C-alkyl, 3-7C-cycloalkyl or 3-7C-cycloalkylmethyl,
or R22 and R23 together and with inclusion of the nitrogen atom to which they are bonded, form a 1-pyrrolidinyl-, 1-piperidinyl-, 1-piperazinyl, 1-(1-4C-alkyl)-piperazin-4-yl-, 1-hexahydroazepinyl-, 4-morpholinyl, 4-thiomorpholinyl-, thiomorpholin-1-oxide-4-yl-, thiomorpholin-1,1-dioxide-4-yl-, pyrrolidin-2,5-dione-1-yl-, morpholin-3,5-dione-4-yl-, piperidin-2,6-dione-1-yl, 4,4-dimethyl-piperidin-2,6-dione-1-yl or a 1-methyl-imidazolidine -2,4-dione-3-yl-ring or a isoindol-1,3-dione-2-yl-ring-system,
n is an integer from 1 to 4,
m is an integer from 1 to 4,
or a salt thereof.

2. A compound of formula 1 according to claim 1, in which
R1 is 1-4C-alkyl,
R2 is 1-4C-alkyl,
R3 represents a phenyl derivative of formulae (a)

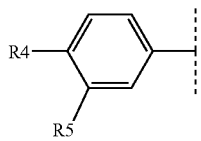

wherein
R4 is 1-2C-alkoxy or 1-2C-alkoxy which is completely or predominantly substituted by fluorine,
R5 is 1-2C-alkoxy or 1-2C-alkoxy which is completely or predominantly substituted by fluorine,
R9 is —C(O)—R10, —S(O)$_2$—R14, —(CH$_2$)$_n$—C(O)—R18 or —C(O)—(CH$_2$)$_m$—R21,
R10 is phenyl or phenyl substituted by R13,
R13 is 1-4C-alkyl or 1-4C-alkoxy,
R14 is —N(R15)R16, phenyl or phenyl substituted by R17,
R15 is hydrogen or 1-4C-alkyl,
R16 is hydrogen or 1-4C-alkyl,
R17 is halogen, nitro, cyano, 1-4C-alkyl, 1-4C-alkoxy or 1-4C-alkoxy which is completely or predominantly substituted by fluorine,
R18 is —N(R19)R20,
R19 is hydrogen or 1-4C-alkyl,
R20 is hydrogen or 1-4C-alkyl,
or R19 and R20 together and with inclusion of the nitrogen atom to which they are bonded, form a 1-pyrrolidinyl-, 1-piperidinyl-, 1-piperazinyl, 1-(1-4C-alkyl)-piperazin-4-yl-, 1-hexahydroazepinyl-, 4-morpholinyl or 4-thiomorpholinyl-ring,
R21 is —N(R22)R23,
R22 is hydrogen or 1-4C-alkyl,
R23 is hydrogen or 1-4C-alkyl,
or R22 and R23 together and with inclusion of the nitrogen atom to which they are bonded, form a 1-pyrrolidinyl-, 1-piperidinyl-, 1-piperazinyl, 1-(1-4C-alkyl)-piperazin-4-yl-, 1-hexahydroazepinyl-, 4-morpholinyl, 4-thiomorpholinyl-, pyrrolidin-2,5-dione-1-yl-, morpholin-3,5-dione-4-yl-, piperidin-2,6-dione-1-yl, 4,4-dimethyl-piperidin-2,6-dione-1-yl or a 1-methyl-imidazolidine-2,4-dione-3-yl-ring or a isoindol-1,3-dione-2-yl-ring-system,
n is an integer from 1 to 4,
m is an integer from 1 to 4,
or a salt thereof.

3. A compound of formula 1 according to claim 1, in which
R1 is methyl or ethyl,
R2 is methyl or ethyl,
R3 represents a phenyl derivative of formulae (a)

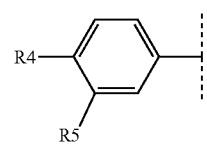

wherein
R4 is methoxy, ethoxy or difluoromethoxy,
R5 is methoxy, ethoxy or difluoromethoxy,
R9 is —C(O)—R10,
R10 is phenyl or phenyl substituted by R13,
R13 is 1-4C-alkyl or 1-4C-alkoxy,
or a salt thereof.

4. A compound of formula 1 according to claim 1, in which
R1 is methyl or ethyl,
R2 is methyl or ethyl, R3 represents a phenyl derivative of formulae (a)

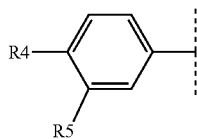

wherein
R4 is methoxy, ethoxy or difluoromethoxy,
R5 is methoxy, ethoxy or difluoromethoxy,
R9 is —S(O)₂—R14,
R14 is —N(R15)R16, phenyl or phenyl substituted by R17,
R15 is hydrogen or 1-4C-alkyl,
R16 is hydrogen or 1-4C-alkyl,
R17 is halogen, nitro, cyano, 1-4C-alkyl, 1-4C-alkoxy or 1-4C-alkoxy which is completely or predominantly substituted by fluorine,
or a salt thereof.

5. A compound of formula 1 according to claim 1, in which
R1 is methyl or ethyl,
R2 is methyl or ethyl,
R3 represents a phenyl derivative of formulae (a)

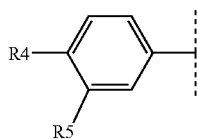

wherein
R4 is methoxy, ethoxy or difluoromethoxy,
R5 is methoxy, ethoxy or difluoromethoxy,
R9 is —(CH₂)ₙ—C(O)—R18,
R18 is —N(R19)R20,
R19 is hydrogen or 1-4C-alkyl,
R20 is hydrogen or 1-4C-alkyl,
or R19 and R20 together and with inclusion of the nitrogen atom to which they are bonded, form a 1-pyrrolidinyl-, 1-piperidinyl-, 1-piperazinyl, 1-(1-4C-alkyl)-piperazin - 4-yl-, 1-hexahydroazepinyl-, 4-morpholinyl or 4-thiomorpholinyl-ring,
n is 1 or 2,
or a salt thereof.

6. A compound of formula 1 according to claim 1, in which
R1 is methyl or ethyl,
R2 is methyl or ethyl,
R3 represents a phenyl derivative of formulae (a)

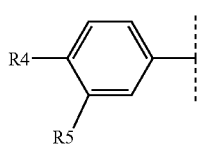

wherein
R4 is methoxy, ethoxy or difluoromethoxy,
R5 is methoxy, ethoxy or difluoromethoxy,
R9 is —C(O)—(CH₂)ₘ—R21,
R21 is —N(R22)R23,
R22 is hydrogen or 1-4C-alkyl,
R23 is hydrogen or 1-4C-alkyl,
or R22 and R23 together and with inclusion of the nitrogen atom to which they are bonded, form a 1-pyrrolidinyl-, 1-piperidinyl-, 1-piperazinyl, 1-methyl-piperazin-4-yl-, 1-hexahydroazepinyl-, 4-morpholinyl, 4-thiomorpholinyl-, pyrrolidin-2,5-dione-1-yl-, morpholin-3,5-dione-4-yl-, piperidin-2,6-dione-1-yl, 4,4-dimethyl-piperidin-2,6-dione-1-yl or a 1-methyl-imidazolidine-2,4-dione-3-yl -ring or a isoindol-1,3-dione-2-yl-ring-system,
m is 1,
or a salt thereof.

7. A compound of formula 1 according to claim 1, in which
R1 is methyl or ethyl,
R2 is methyl or ethyl,
R3 represents a phenyl derivative of formulae (a)

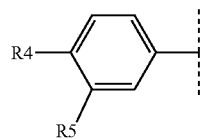

wherein
R4 is methoxy or ethoxy,
R5 is methoxy or ethoxy,
R9 is —C(O)—R10,
R10 is phenyl or phenyl substituted by R13,
R13 is methoxy,
or a salt thereof.

8. A compound of formula 1 according to claim 1, in which
R1 is methyl or ethyl,
R2 is methyl or ethyl,
R3 represents a phenyl derivative of formulae (a)

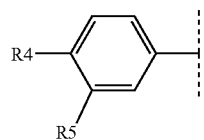

wherein
R4 is methoxy or ethoxy,
R5 is methoxy or ethoxy,
R9 is —S(O)₂—R14,
R14 is —N(R15)R16, phenyl or phenyl substituted by R17,
R15 is methyl,
R16 is methyl,
R17 is cyano, methyl, methoxy or trifluoromethoxy,
or a salt thereof.

9. A compound of formula 1 according to claim 1, in which
R1 is methyl or ethyl,
R2 is methyl or ethyl, R3 represents a phenyl derivative of formulae (a)

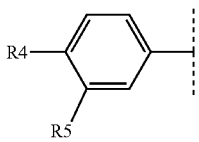

wherein
R4 is methoxy or ethoxy,
R5 is methoxy or ethoxy,
R9 is —(CH$_2$)$_n$—C(O)—R18,
R18 is —N(R19)R20,
R19 is hydrogen,
R20 is hydrogen,
or R19 and R20 together and with inclusion of the nitrogen atom to which they are bonded, form a 4-morpholinyl-ring,
n is 1 or 2,
or a salt thereof.

10. A compound of formula 1 according to claim 1, in which
R1 is methyl or ethyl,
R2 is methyl or ethyl,
R3 represents a phenyl derivative of formulae (a)

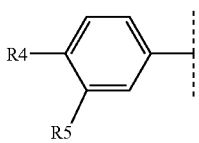

wherein
R4 is methoxy or ethoxy,
R5 is methoxy or ethoxy,
R9 is —C(O)—(CH$_2$)$_m$—R21,
R21 is —N(R22)R23,
or R22 and R23 together and with inclusion of the nitrogen atom to which they are bonded, form a 1-methyl-piperazin-4-yl-, pyrrolidin-2,5-dione-1-yl- or a morpholin-3,5-dione-4-yl-ring or a isoindol-1,3-dione-2-yl-ring-system,
m is 1,
or a salt thereof.

11. A compound of formula 1 according to claim 1, in which
R1 is 1-4C-alkyl and
R2 is 1-4C-alkyl,
R3 represents a phenyl derivative of formulae (a)

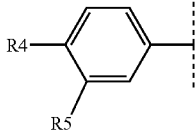

wherein
R4 is 1-4C-alkoxy or 1-4C-alkoxy which is completely or predominantly substituted by fluorine, R5 is 1-8C-alkoxy, 3-7C-cycloalkoxy, 3-7C-cycloalkylmethoxy, or 1-4C-alkoxy which is completely or predominantly substituted by fluorine,
R9 is —C(O)R10, —S(O)$_2$—R14, —(CH$_2$)$_n$—C(O)—R18 or —C(O)—(CH$_2$)$_m$—R21, R10 is 1-4C-alkyl, —N(R11)R12, phenyl or phenyl substituted by R13,
R11 is hydrogen, 1-4C-alkyl, 3-7C-cycloalkyl or 3-7C-cycloalkylmethyl,
R12 is hydrogen, 1-4C-alkyl, 3-7C-cycloalkyl or 3-7C-cycloalkylmethyl,
or R11 and R12 together and with inclusion of the nitrogen atom to which they are bonded, form a 1-pyrrolidinyl-, 1-piperidinyl-, 1-piperazinyl, 1-(1-4C-alkyl)-piperazin-4-yl-, 1-hexahydroazepinyl-, 4-morpholinyl, 4- thiomorpholinyl-, thiomorpholin-1-oxide-4-yl- or thiomorpholin-1,1-dioxide-4-yl-ring,
R13 is hydroxyl, halogen, nitro, cyano, hydroxycarbonyl, 1-4C-alkyl, trifluoromethyl, 1-4C-alkoxy, 1-4C-alkoxy which is completely or predominantly substituted by fluorine, 1-4C-alkoxycarbonyl, amino, mono- or di-1-4C-alkylamino, aminocarbonyl, mono- or di1-4C-alkylaminocarbonyl, 1-4C-alkylcarbonyl, 1-4C-alkylcarbonylamino or 1-4C-alkylcarbonyloxy,
R14 is 1-4C-alkyl, —N(R15)R16, phenyl or phenyl substituted by R17,
R15 is hydrogen, 1-4C-alkyl, 3-7C-cycloalkyl or 3-7C-cycloalkylmethyl,
R16 is hydrogen, 1-4C-alkyl, 3-7C-cycloalkyl or 3-7C-cycloalkylmethyl,
or R15 and R16 together and with inclusion of the nitrogen atom to which they are bonded, form a 1-pyrrolidinyl-, 1-piperidinyl-, 1piperazinyl, 1-(1-4C-alkyl)-piperazin-4-yl-, 1-hexahydroazepinyl-, 4-morpholinyl, 4-thiomorpholinyl-, thiomorpholin-1-oxide-4-yl- or thiomorpholin-1,1-dioxide-4-yl-ring,
R17 is hydroxyl, halogen, nitro, cyano, carboxyl, 1-4C-alkyl, trifluoromethyl, 1-4C-alkoxy, 1-4C-alkoxy which is completely or predominantly substituted by fluorine, 1-4C-alkoxycarbonyl, amino, mono- or di-1-4C-alkylamino, aminocarbonyl, mono- or di-1-4C-alkylaminocarbonyl, 1-4C-alkylcarbonyl, 1-4C-alkylcarbonylamino or 1-4C-alkylcarbonyloxy,
R18 is —N(R19)R20,
R19 is hydrogen, 1-4C-alkyl, 3-7C-cycloalkyl or 3-7C-cycloalkylmethyl,
R20 is hydrogen, 1-4C-alkyl, 3-7C-cycloalkyl or 3-7C-cycloalkylmethyl,
or R19 and R20 together and with inclusion of the nitrogen atom to which they are bonded, form a 1-pyrrolidinyl-, 1-piperidinyl-, 1-piperazinyl-, 1-(1-4C-alkyl)-piperazin-4-yl-, 1-hexahydroazepinyl-, 4-morpholinyl, 4-thiomorpholinyl-, thiomorpholin-1-oxide-4-yl- or thiomorpholin-1,1 -dioxide-4-yl-ring,
R21 is —N(R22)R23,
R22 is hydrogen, 1-4C-alkyl, 3-7C-cycloalkyl or 3-7C-cycloalkylmethyl,
R23 is hydrogen, 1-4C-alkyl, 3-7C-cycloalkyl or 3-7C-cycloalkylmethyl,
or R22 and R23 together and with inclusion of the nitrogen atom to which they are bonded, form a 1-pyrrolidinyl-, 1-piperidinyl-, 1piperazinyl, 1 -(1-4C-alkyl)-piperazin-4-yl-, 1-hexahydroazepinyl-, 4-morpholinyl, 4-thiomorpholinyl-, thiomorpholin-1-oxide-4-yl-, thiomorpholin-1,1-dioxide-4-yl- or a pyrrolidin-2,5-dione-1-yl-ring, n is an integer from 1 to 4,
m is an integer from 1 to 4,
or a salt thereof.

12. A compound of formula 1 according to claim 1, in which
R1 is 1-4C-alkyl,
R2 is 1-4C-alkyl,
R3 represents a phenyl derivative of formulae (a)

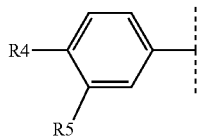

(a)

wherein
R4 is 1-2C-alkoxy or 1-2C-alkoxy which is completely or predominantly substituted by fluorine,
R5 is 1-4C-alkoxy,
R9 is —S(O)$_2$—R14, —(CH$_2$)$_n$—C(O)—R18 or —C(O)—(CH$_2$)$_m$—R21,
R14 is phenyl or phenyl substituted by R17,
R17 is halogen, nitro, cyano, 1-4C-alkyl or 1-4C-alkoxy,
R18 is —N(R19)R20,
R19 is hydrogen or 1-4C-alkyl,
R20 is hydrogen or 1-4C-alkyl,
or R19 and R20 together and with inclusion of the nitrogen atom to which they are bonded, form a 1-pyrrolidinyl-, 1-piperidinyl-, 1-piperazinyl, 1-(1-4C-alkyl)-piperazin -4-yl-, 1-hexahydroazepinyl-, 4-morpholinyl or 4-thiomorpholinyl-ring,
R21 is —N(R22)R23,
R22 is hydrogen or 1-4C-alkyl,
R23 is hydrogen or 1-4C-alkyl,
or R22 and R23 together and with inclusion of the nitrogen atom to which they are bonded, form a 1-pyrrolidinyl-, 1-piperidinyl-, 1-piperazinyl, 1-(1-4C-alkyl)-piperazin-4-yl-, 1-hexahydroazepinyl-, 4-morpholinyl, 4-thiomorpholinyl- or a pyrrolidin-2,5-dione-1-yl-ring,
n is an integer from 1 to 4,
m is an integer from 1 to 4,
or a salt thereof.

13. A compound of formula 1 according to claim 1, in which
R1 is methyl,
R2 is methyl,
R3 represents a phenyl derivative of formula (a)

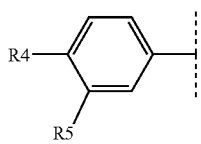

(a)

wherein
R4 is methoxy or ethoxy,
R5 is methoxy or ethoxy,
R9 is —S(O)$_2$—R14, —(CH$_2$)$_n$—C(O)R18 or —C(O)—(CH$_2$)$_m$—R21,
R14 is 2-cyanophenyl,
R18 is amino or 4-morpholinyl,
R21 is pyrrolidin-2,5-dione-1-yl,
n is 1 or 2,
m is 1,
or a salt thereof.

14. A pharmaceutical composition comprising one or more compounds according to claim 1, or a pharmaceutically acceptable salt thereof, together with a pharmaceutically acceptable auxiliary and/or carrier.

* * * * *

UNITED STATES PATENT AND TRADEMARK OFFICE
CERTIFICATE OF CORRECTION

PATENT NO.         : 7,494,990 B2
APPLICATION NO. : 10/587836
DATED                 : February 24, 2009
INVENTOR(S)       : Wiro M. P. B. Menge et al.

It is certified that error appears in the above-identified patent and that said Letters Patent is hereby corrected as shown below:

Claim 1, Column 28, Line 56,

Please delete "1-pyrrohidinyl-,"
and
replace with

-- 1-pyrrolidinyl-, --

Claim 1, Column 28, Line 58,

Please delete "4-morphohinyl,"
and
replace with

-- 4-morpholinyl-, --

Claim 1, Column 28, Lines 58-59,

Please delete "4-thio-morphohinyl-, thiomorphohin-1-oxide-4yl- or"
and
replace with -- 4-thio-morpholinyl-, thiomorpholin-1-oxide-4yl- or --

Claim 11, Column 34, Lines 21-22,

Please delete "di1-4C-alky-laminocarbonyl,"
and
replace with

-- di-1-4C-alky-laminocarbonyl, --

UNITED STATES PATENT AND TRADEMARK OFFICE
CERTIFICATE OF CORRECTION

PATENT NO. : 7,494,990 B2
APPLICATION NO. : 10/587836
DATED : February 24, 2009
INVENTOR(S) : Wiro M. P. B. Menge et al.

It is certified that error appears in the above-identified patent and that said Letters Patent is hereby corrected as shown below:

Claim 11, Column 34, Line 33,

Please delete "1piperazinyl,"
and
replace with

-- 1-piperazinyl, --

Claim 11, Column 34, Line 63,

Please delete "1piperazinyl,"
and
replace with

-- 1-piperazinyl, --

Signed and Sealed this

Twenty-sixth Day of May, 2009

JOHN DOLL
*Acting Director of the United States Patent and Trademark Office*